(12) United States Patent
Wallach et al.

(10) Patent No.: US 7,745,579 B1
(45) Date of Patent: Jun. 29, 2010

(54) INHIBITOR OF NF-KB ACTIVATION

(76) Inventors: David Wallach, 24 Borochov Street, Rehovot (IL) 76406; Andrei Kovalenko, Beit Clore, Weizmann Institute of Science, Rehovot (IL) 76100; Giuseppina Cantarella, Institute of Pharmacology School of Medicine Univeristy of Catania, Catania (IT) I-95025

( * ) Notice: Subject to any disclaimer, the term of this patent is extended or adjusted under 35 U.S.C. 154(b) by 1904 days.

(21) Appl. No.: 09/671,687

(22) Filed: Sep. 28, 2000

Related U.S. Application Data

(63) Continuation-in-part of application No. 09/646,403, filed as application No. PCT/IL99/00158 on Mar. 18, 1999, now Pat. No. 6,734,174.

(30) Foreign Application Priority Data

Sep. 1, 1998 (IL) ...................................... 126024
Feb. 17, 2000 (IL) ...................................... 134604

(51) Int. Cl.
*C07K 14/47* (2006.01)
*C07K 16/18* (2006.01)

(52) U.S. Cl. ................. 530/350; 530/387.1; 530/387.3; 530/387.9; 530/388.1; 536/23.5; 536/23.53

(58) Field of Classification Search ................. 530/350, 530/387.1, 387.3, 388.1; 424/130.1, 133.1, 424/134.1, 139.1, 141.1, 142.1, 152.1, 138.1, 424/150.1

See application file for complete search history.

(56) References Cited

U.S. PATENT DOCUMENTS

2005/0003447 A1* 1/2005 Lal et al. ........................ 435/6

FOREIGN PATENT DOCUMENTS

| WO | 96 25941 | 8/1996 |
|---|---|---|
| WO | 96 36730 | 11/1996 |
| WO | 97 15586 | 5/1997 |
| WO | 97 45542 | 12/1997 |
| WO | WO 99/47672 A1 | 9/1999 |
| WO | 0017355 A2 | 3/2000 |

OTHER PUBLICATIONS

Ghosh and Karin. Missing pieces in the NF-kB puzzle. Apr. 2002. Cell 109: S81-S96.*
Baldwin. The transcription factor NF-kB and human disease. Jan. 2001. The Journal of Clinical Investigation 107:3-6.*
Everett et al. Pendred syndrome is caused by mutations in a putative sulphate transporter gene (PDS). Nature Genetics 17: 411-422, 1997.*
Scott et al. The pendred syndrome gene encodes a chloride-iodide trasnport protein. Nature Genetics 21: 440-443, 1999.*
Berendsen H.J.C. A glimpse of the Holy Grail? Science 282: 642-643, 1998.*
Bignell et al. Nature Genetics 25: 160-165, Jun. 2000.*
Nagase et al. DNA Research 5: 355-364, Dec. 1998.*
Stratton, M.R., Genbank submission AJ250014, 3 pages, Nov. 29, 1999.*
USPTO Sequence Search, Result 7 from .rge database, pp. 12-14.*
Rothwarf et al., "IKK- is an essential regulatory subunit of the $I_KB$ kinase complex", *Nature*, (1998) vol. 395, No. 17, pp. 297-300.
Yamaoka et al., "Complementation Cloning of NEMO, a Component of the $I_KB$ Kinase Complex Essential for NF-$_KB$ Activation", *Cell*, (1998), vol. 93, pp. 1231-1240.
Li et al., "Identification of a cell protein (FIP-3) as a modulator of NF-$_KB$ activity and as a target of an adenovirus inhibitor of tumor necrosis factor α-induced apoptosis", *Proc. Natl. Acad. Sci, USA*, vol. 96, pp. 1042-1047.
Li et al., "Interaction of an Adenovirus E3 14.7-Kilodalton Protein with a Novel Tumor Necrosis Factor Alpha-Inducible Cellular Protein Containing Leucine Zipper Domains", *Molecular and Cellular Biology*, (1998), vol. 18, No. 3, pp. 1601-1610.
May et al, "Signal transduction through NF-kappaβ", *Immunology Today* 19:80-88(1998).
"*Homo sapiens* mRNA for KIAA0849 protein, partial cds", *EMBL Nucleotide Sequence* XP-002108972 (Feb. 9, 1999).
Ye et al. "The structural basis for the recognition of diverse receptor sequences by TRAF2" Molecular Cell, 4:321-330 (1999).

* cited by examiner

*Primary Examiner*—Eileen B O Hara
(74) *Attorney, Agent, or Firm*—Browdy and Neimark, PLLC

(57) ABSTRACT

The present invention relates to a protein, designated NAP (Nemo Associated Protein), that was discovered to inhibit the activation of transcription factor NF-kB by various signals that are important in inflammatory and immune processes. The DNA and the recombinant production of this protein is also disclosed as well as methods of using the protein or encoding DNA.

17 Claims, 4 Drawing Sheets

FIG. 1

```
   1 GGGGTTTCT TTTACACTC TCGGTACCG AACTCGGATC CACTAGTAAC GGGCCGCCAG TGTGCTGGAA ATTCGGCACG AGGGTGTGG GAGCCGGGGC 100
 101 CGGCCCGGGA CGCGGCTGG GAAGCCGGG CGAGGGGCGA CGCCCGCC CCCCTTCTA GGGTGAGGAT GGTTCTACAC AGCCACCCGG 200
 201 AGTTCCTTAG TTGAAAGGTG CGCCCCTGCT TGACAGAATG TGGTAATTGT AAACATATT TCCTGATCAT CTTTCCATTG 300
 301 TCTTTCATGGA AAATTGATAA ATATTTGTGC CTTCCAACTC TCGTCTTGGT TGAATGACTT CATCTTAATA CAACATGGAC ACCACGTTGC TGAAACATG 400
 401 CTTTCATGGACT GCCACTGAAT TTATCTTTG CGGTTTATG ACAAAGTTAT TAGTAGTTTC CCTTTTTGA ATTAGTATT TGAAGTTAAT ATCACAATGA 500
 501 GTTCAGGCTT ATGGAGCCAA GAAAAGTCA CTTCACCCTA CTGGGAAGAG CGGATTTT ACTTGCTTCT TCAAGAATGC AGCCGTTACAG ACAAACAAAC 600
 601 ACAAAAGTC CTTAAAGTAC CGAAGGGAAG TATAGGACAG TATATTCAAG ATCGTTCTGT GGGGCATTCA AGGATTCCTT CTGCAAAAGG CAAGAAAAT 700
 701 CAGATTGGAT TAAAAATTCT AGAGCAACCT CATGCAGTTC TCTTGTTGA TGAAACGGAT GTTGTAGAGA TAAATGAAAA GTTCACAGAG TTACTTTTGG 800
 801 CAATTACCAA TTGGAGGAG AGGTTCAGCC TGTTTAAAA CAGAAACAGA CTAAGTAAAG GCCTCCAAAT AGACGTGGCC TGTCCTGTGA AAGTACAGCT 900
 901 GAGATCTGGG GAAGAAAAAT TTCCTGGAGT TGTAGCAGA GAGGACAGTC TCCGGAATAT TCTTTGGAGT TGAATTGCTG 1000
1001 GAAGAAGGTC GTGGTCAAGG TTTCACTGAC GGGGTGTACC AAGGGAAACA GCTTTTTCAG TGTGATGAAG ATTGTGGCGT CCTTTGTCCT GTTTGTTGCA TTGGACAAGC 1100
1101 TAGAACTCAT AGAAGATGAT GACACTGCAT TGAAAGTGA TTACGCAGGT CAAAATCTCT CGAACTTCCT CCTTTGGAAA TAAACTCCAG 1200
1201 AGTTTCTTG AAGGGGTGGAG AAACAATAGA ATCTGGAACA GTTATATTCT GTGATGTTTT GCCAGGGAAAA GAAAGCTTAG AGTATTGTT TGGTCTGTGAC 1300
1301 ATGGATAACC CTATTGGCAA CTGGGATGGA AGATTTGATG GAGTGCACT TTGTAGTTTT GCGTGTGTG AAGTACAAT TCTATTGCAC ATCAATGATA 1400
1401 TCATCCCAGA GAGTGTGACG CAGGAAAGGA CGCCTCCCAA ACTTGCCTTT ATGTCAAGAG GTGTTGGGGA CAAAGGTTCA TCCAGTACTA ATAAACCAAA 1500
1501 GGCTACAGGA TCTACCTCAG ACCCTGTAAA TAGAAMCAGA TCTGAATTAT TTTATACCTT TACAGAGATA TCTGTTGACT CACAACCACA ATCCAAATCA 1600
1601 AAAAATACAT GGTACATTGA GAAGTTGCA GAAGACCCTG CAAAATCTCT CAAATCTCT GGAACTTCCT TTGACCGTTC TTCCAGGCTC CTCCAGGCCT 1700
1701 CTCCGTGAA CTCACTGACC ACCGAGAACA GATTCCACTC TTTACCATTC AGTCTCACCA AGATGCCCAA TACCAATGGA AGTCCTCCTG ACAGTCCAACT 1800
1801 TCTTCTCTGTCA GCCCAGTCTG TAATGGAAGA GCTAAACACT GCAAGTCTC ACCCCGTCC AAGAGAGTCC ATGCCTCCTG GGAACTCACA TGGTCTAGAA 1900
1901 GTGGCTCAT TGGCTGAAGT TAAGGAGTAAC CCTCCTTTCT ATGGGGTAAT CCGTTGGATC GGTCAGCGAC CAGGACTGAA TGAAGTGCTC GCTGGACTGC 2000
2001 AACTGGAAGA TGAGTGTGCA GGCTGTGCA CCTGTGCCCT CAGAGGCACT GGTATTTCA CCTGTGCCCT GAAGAAGGCG CTGTTGTGA AACTGAAGAG 2100
2101 CTGCAGGCCT GACTCTAGGT TTGCATCATT GCAGCCGGTT TCCAATCAGA TGAGCGCTG TAACTCTTTA GCATTGGAG GCTACTTAAG TGAAGTAGTA 2200
2201 GAAGAAATA CTCCACCAAA AATGGAAAAAA GAAGGCTTGG AGATAATGAT TGGGAAGAAG AAAGGCATCC AGGGTCATTA CAATTCTGT TACTTAGACT 2300
2301 CAACCTTATT GCTTTAGTT CTGTTCTGGA CACTGTGTA CTTAGACCCA AAGAAAAGAA CGATGTAGAA TATTATAGTG AACCCAAGA 2400
```

FIG. 2A

```
2401 GCTACTGAGG ACAGAAATTG TTAATCCTCT GAGAATATAT GGATATGTGT GTGCCACAAA AATTATGAAA CTGAGGAAAA TACTTGAAAA GGTGGAGGCT 2500
2501 GCATCAGGAT TTACCTCTGA AGAAAAAGAT CCTGAGGAAT TCTTGAATAT TCTGTTTCAT CATATTTTAA GGGTAGAACC TTTGCTAAAA ATAAGATCAG 2600
2601 CAGGTCAAAA GGTACAAGAT TGTTACTTCT ATCAAATTTT TATGGAAAAA AATGAGAAAG TTGGCGTTCC CACAATTCAG CAGTTGTTAG AATGGTCTTT 2700
2701 TATCAACAGT AACCTGAAAT TTGCAGAGGC ACCATCATGT CTGATTATTC AGATGCCTCG ATTTGGAAAA GACTTTAAAC TATTTAAAAA AATTTTTCCT 2800
2801 TCTCTGGAAT TAAATATAAC AGATTTACTT GAAGACACTC CCAGACAGTG CCGGATATGT GGAGGGCTTG CAATGTATGA GTGTAGAGAA TGCTACGACG 2900
2901 ATCCGGACAT CTCAGCTGGA AAAATCAAGC AGTTTTGTAA AACCTGCAAC ACTCAAGTCC GAAGAGGCTG AATCATAAAT ATAACCCAGT 3000
3001 GTCACTTCCC AAAGACTTAC CCGACTGGGA CTGGAAGCAC GGCTGCATCC CTTGCCAGAA TATGGAGTTA TTTGCTGTTC TCTGCATAGA AACAAGCCAC 3100
3101 TATGTTGCTT TTGTTGACTT ATGCCCAGAA GTAGGAGAGT ACTTGAAGAT GTTCTGGACTC TGAACAGCAT CCTTGAAGAG GCCGATCGGG ATGGTGGTCA GAATGGCTTC AACATTCCTC 3200
3201 AAGTCACTCC ATGCCCAGAA GTAGGAGAGT ACTTGAAGAT GTTCTGCAAA GACCTGCATT CCTTGGACTC CAGGAGAATC CAAGGCTGTG CAGGAAGACT 3300
3301 GCTTTGTGAT GCATATATGT TCTTATTCGA GAGTCCAACA ATGAGTTTGT ACAAATAACT GGGGTCATCG GGAAAGGCAA AGAAACTGAA GGCAGAGTCC 3400
3401 TAACGTTGCA TCTTTATTCGA GCTGGCAGTT CTGTTCACGT CCAATGGATGT CTTTGTGGTG ATGATCCTTC AGAAAAGGAT GCCTCTGTTT 3500
3501 AAAAACAAAT TGCTTTTGTG TCCCTGAAGT ATTAAGTCAC CACTCAGAA AGTATGTTTG TGTTGGTTTT TTAAGAAGTC TAAATGAAGT 3600
3601 TATTAATACC TGAAGGTTTA AGTAAGTGC ATTGATCATA TGATATTTT GGAAGCATAC AATTTTAATT GTGGAAGTTT AAGCCTCTT TTAGTCCATT 3700
3701 GAGAATGTAA ATAAA                                                                                              3715
```

FIG. 2B

|     |            |            |            |            |            |            |            |            |            |            |     |
| --- | ---------- | ---------- | ---------- | ---------- | ---------- | ---------- | ---------- | ---------- | ---------- | ---------- | --- |
| 8   | MSS        | GLWSQEKVTS | PYWEERIFYL | LLQECSVTDK | QTQKLLKVPK | SVGHSRIPSA | KGKKNQIGLK | ILEQHAVLF  | VDEDVVEINE | 100 |
| 101 | KFTELLLAIT | NCEERFSLFK | NRNRLSKGLQ | IDVGCPVKVQ | LRSGEEKFPG | ERTVSGIFFG | VELLEEGRGQ | GFTDGVYQGK | QLFQCDEDCG | 200 |
| 201 | FVALDKLEL  | IEDDDTALES | DYAGPGDTMQ | VELPPLEINS | RVSLKGGETI | ESGTVIFCDV | LPGKESLGYF | VGVDMDNPIG | NWDGRFDGVL | CSFACVESTI | 300 |
| 301 | LLHINDIIPE | SVTQERRPPK | LAEMSRGVGD | KGSSSHNKPK | ATGSTSDFGN | RRSELFYTLN | GSSVDSQPQS | KSKNTWYIDE | VAEDPAKSLT | EISTDFDRSS | 400 |
| 401 | PPLQPPVNS  | LTTENRFHSL | PFSLTKMPNT | NGSIGHSPLS | LSAQSVMEEL | NTAPVQESPP | LAMPPGNSHG | LEVGSLAEVK | ENPPFYGVIR | WIGQPPGLNE | 500 |
| 501 | VLAGLELEDE | CAGCTDGTFR | GTRYFTCALK | KALFVKLKSC | RPDSRFASLQ | PVSNQIERCN | SLAFGGYLSE | VVEENTPPKM | EKEGLEIMIG | KKKGTQGHYN | 600 |
| 601 | SCYLDSTLFC | LFAFSSVLDT | VLLRPKEKND | VEYYSETQEL | LRTEIVNPLR | IYGYVCATKI | MKLRKILEKV | EAASGFTSEE | KDPEEFLNIL | FHHILRVEPI, | 700 |
| 701 | LKIRSAGQKV | QDCYFYQIFM | EKNEKVGVPT | IQQLLEWSFI | NSNLKFAEAP | SCLIIQMPRF | GKDFKLFKKI | FPSLELNITD | LLEDTPRQCR | ICGGLAMYEC | 800 |
| 801 | RECYDDPDIS | AGKIKQFCKT | CNTQVHLHPK | RLNHKYNPVS | LPKDLPDWDW | RHGCIPCQNM | ELFAVLCIET | SHYVAFVKYG | KDDSAWLFFD | SMADRDGGQN | 900 |
| 901 | GFNIPQVTPC | PEVGEYLKMS | LEDLHSLDSR | RIQGCARRLL | CDAYMCMYQS | PTMSLYK    |            |            |            |            | 957 |

FIG. 3

INHIBITOR OF NF-κB ACTIVATION

CROSS-REFERENCE TO RELATED APPLICATIONS

This is a continuation-in-part of application Ser. No. 09/646,403, filed Sep. 18, 2000, which is a 371 national stage application of International PCT application PCT/IL99/00158, filed Mar. 18, 1999, the contents of which are herein incorporated entirely by reference.

BACKGROUND OF THE INVENTION

1. Field of the Invention

The present invention is concerned with a novel protein that inhibits the activation of transcription factor NF-κB by various signals that are important in inflammatory and immune processes. More particularly the invention relates to a protein herein designated NAP (Nemo Associated Protein), its recombinant production and its use.

2. Description of the Related Art

The Tumor Necrosis Factor/Nerve Growth Factor (TNF/NGF) receptor superfamily is defined by structural homology between the extracellular domains of its members Bazan, (1993). In general, with the exception of two receptors, the p55 TNF receptor and Fas/APO1, the various members of this receptor family do not exhibit clear similarity of structure in their intracellular domains. Nevertheless, there is much similarity of function between the receptors, indicating that they share common signaling pathways. This is seen in the ability of several receptors of the TNF/NGF family to activate the transcription factor NF-κB, by means of a cytoplasmic activator protein, TNF Receptor Associated Factor 2 (TRAF2). TRAF2 exerts its activity by binding to the structurally-dissimilar intracellular domains of several of the receptors of the TNF/NGF family.

TRAF2 is a member of a recently described family of proteins called TRAF (TNF Receptor Associated Factor) that includes several proteins identified as, for example, TRAF1, TRAF2, TRAF3, and TRAF6.

All proteins belonging to the TRAF family share a high degree of amino acid identity in their C-terminal domains, while their N-terminal domains may be unrelated. The TRAF2 molecule contains a ring finger motif and two TFIIIA-like zinc finger motifs at its C-terminal area. The C-terminal half of the molecule includes a region known as the "TRAF domain" containing a potential leucine zipper region extending between amino acids 264-358 (called N-TRAF), and another part towards the carboxy end of the domain between amino acids 359-501 (called C-TRAF) which is responsible for TRAF-binding to the receptors and to other TRAF molecules to form homo- or heterodimers.

Activation of the transcription factor NF-κB is one manifestation of the signaling cascade initiated by some of the TNF/NGF receptors and mediated by TRAF2. NF-κB comprises members of a family of dimer-forming proteins with homology to the Rel oncogene which, in their dimeric form, act as transcription factors. These factors are ubiquitous and participate in regulation of the expression of multiple genes. Although initially identified as a factor that is constitutively present in B cells at the stage of IgK light chain expression, NF-κB is known primarily for its action as an inducible transcriptional activator. NF-κB has many different activities in the cell, most of which are rapidly induced in response to extracellular stimuli. The majority of the NF-κB-activating agents are inducers of immune defense, including components of viruses and bacteria, cytokines that regulate immune response, UV light and others. Accordingly, many of the genes regulated by NF-κB contribute to immune defense (Grilli et al., 1993).

One major feature of NF-κB-regulation is that this factor can exist in a cytoplasmic non-DNA binding form which can be induced to translocate to the nucleus, bind DNA and activate transcription. The switching between these two forms of NF-κB is regulated by I-κB—a family of proteins that contain repeats of a domain that was initially identified in the erythrocyte protein ankyrin (Gilmore et al. 1993). In the unstimulated form, the NF-κB dimer occurs in association with an I-κB molecule which causes retention of the dimer in the cytoplasm and prevents its interaction with the NF-κB-binding DNA sequence and subsequent activation of transcription. The dissociation of I-κB from the NF-κB dimer constitutes the critical step of its activation by many of its inducing agents (DiDonato et al., 1995).

One of the most potent inducing agents of NF-κB is the cytokine tumor necrosis factor (TNF). There are two different TNF receptors, the p55 and p75 receptors, the expression levels of which differ according to cell type (Vandenabeele et al., 1995). The p75 receptor responds preferentially to the cell-bound form of TNF (TNF is expressed both as a beta-transmembrane protein and as a soluble protein) while the p55 receptor responds equally to both forms of TNF (Grell et al., 1995). The intracellular domains of the two receptors are structurally unrelated and bind different cytoplasmic proteins. Nevertheless, at least some of the effects of TNF, including the cytocidal effect of TNF and the induction of NF-κB, can be induced by both receptors. This feature is cell specific. The p55 receptor is capable of inducing a cytocidal effect or activation of NF-κB in all cells that exhibit such effects in response to TNF. The p75-R can have such effects only in some cells. Others, although expressing the p75-R at high levels, show induction of the effects only in response to stimulation of the p55-R (Vandenabeele et al., 1995). Apart from the TNF receptors, various other receptors of the TNF/NGF receptor family: CD30 (McDonald et al., 1995 and Berberich et al., 1994), the lymphotoxin beta receptor and, in a few types of cells, Fas/APO1 (Rensing-Ehl et al. 1995) are also capable of inducing activation of NF-κB. The IL-1 type I receptor, which also effectively triggers NF-κB activation, shares most of the effects of the TNF receptors despite the fact that it has no structural similarity to them.

The activation of NF-κB upon triggering of these various receptors results from induced phosphorylation of its associated I-κB molecules. This phosphorylation tags I-κB for degradation, which most likely occurs in the proteasome. The nature of the kinase that phosphorylates I-κB, and its mechanism of activation upon receptor triggering is still unknown. However, in recent years, there have been some advantages in relation to the identity of three receptor-associated proteins that appear to take part in initiation of the above-mentioned phosphorylation. A protein called TRAF2, initially cloned by D. Goeddel and his colleagues (Rothe, M. et al. 1994) seems to play a central role in NF-κB-activation by the various receptors of the TNF/NGF family. The protein, which when expressed at high levels can by itself trigger NF-κB activation, binds to activated p75 TNF-R, lymphotoxin beta receptor (Mosialos et al. 1995), CD40 (Rothe et al., 1995) and CD-30 (unpublished data) and mediates the induction of NF-κB by them. TRAF2 does not bind to the p55 TNF receptor nor to Fas/APO1, however, it can bind to a p55 receptor-associated protein called TRADD and TRADD has the ability to bind to a Fas/APO1-associated protein called MORT1 (or FADD). Another receptor-interacting protein, called RIP (Stanger et al., 1995) is also capable of interacting with TRAF2 as well as with FAS/APO1, TRADD, the p55 TNF receptor and MORT-1. Thus, while RIP has been associated with cell cytotoxicity induction (cell death), its ability to interact with TRAF2 also implicates it in NF-κB activation and it also may serve in addition to augment the interaction between FAS/APO1, MORT-1, p55 TNF receptor and TRADD with TRAF2 in the pathway leading to NF-κB activation. These associations apparently allow the p55 TNF receptor and Fas/APO1 to trigger NF-κB activation (Hsu et al., 1995). A protein called RAP-2 (RIP associated protein-2), now known as NEMO, is disclosed in WO 99/47672.

The triggering of NF-κB activation by the IL-1 receptor occurs independently of TRAF2 and may involve a recently-cloned IL-1 receptor-associated protein-kinase called IRAK (Croston et al., 1995).

By what mechanism TRAF2 acts is not clear. Several cytoplasmic molecules that bind to TRAF2 have been identified. However, the mechanisms by which TRAF2, which by itself does not possess any enzymatic activity, triggers the phosphorylation of I-κB is still uncertain.

In addition, it is to be noted that TRAF2 also binds to the p55 (CD120a) and p75 (CD120b) TNF receptors, as well as to several other receptors of the TNF/NGF receptor family, either directly or indirectly via other adaptor proteins as noted above. TRAF2 is thus crucial for the activation of NF-κB (Wallach, 1996). However, TRAF3 actually inhibits activation of NF-κB by some receptors of the TNF/NGF family, whilst TRAF6 is required for induction of NF-κB by IL-1 (Cao et al. 1996).

It is now known that TNF and the FAS/APO1 ligand, for example, can have both beneficial and deleterious effects on cells. TNF, for example, contributes to the defense of the organism against tumors and infectious agents and contributes to recovery from injury by inducing the killing of tumor cells and virus-infected cells, augmenting the antibacterial activities of granulocytes, and thus, in these cases the TNF-induced cell killing is desirable. However, excess TNF can be deleterious and as such may play a major pathogenic role in a number of pathological states such as septic shock, anorexia, rheumatic diseases, inflammation and graft-vs-host reactions. In such cases the TNF-induced cell killing has a deleterious effect. The FAS/APO1 ligand, for example, also has both desirable and deleterious effects. Binding of this ligand to its receptor induces the killing of autoreactive T cells during maturation of T cells, i.e. the killing of T cells which recognize self-antigens, during their development, thereby preventing the occurrence of autoimmune diseases. Further, various malignant cells and HIV-infected cells carry the FAS/APO1 receptor on their surface and can thus be destroyed by activation of this receptor by its ligand or by antibodies specific thereto, and thereby activation of cell death (apoptosis) intracellular pathways mediated by this receptor. However, the FAS/APO1 receptor may mediate deleterious effects, for example, uncontrolled killing of tissue which is observed in certain diseases such as acute hepatitis that is accompanied by the destruction of liver cells.

NF-κB is known to control the expression of many immune- and inflammatory-response genes. Thus, in view of the fact that the TNF/NGF family of receptors can induce cell survival pathways (via NF-κB induction) on the one hand and can induce cell death pathways on the other hand, there apparently exists a fine balance, intracellularly between these two opposing pathways. For example, when it is desired to achieve maximal destruction of cancer cells or other infected or diseased cells, it would be desired to have TNF and/or the FAS/APO1 ligand inducing only the cell death pathway without inducing NF-κB. Conversely, when it is desired to protect cells such as in, for example, inflammation, graft-vs-host reactions, acute hepatitis, it would be desirable to block the cell killing induction of TNF and/or FAS/APO1 ligand and enhance, instead, their induction of NF-κB, which would in turn lead to the enhanced expression of many immune- and inflammatory-response genes. Likewise, in certain pathological circumstances it would be desirable to block the intracellular signaling pathways mediated by the p75 TNF receptor and the IL-1 receptor, while in others it would be desirable to enhance these intracellular pathways.

It is an object of this invention to provide clones, proteins, and other tools for the modulation and/or mediation of NF-kB effects, in particular clones comprising the NAP protein and the NAP protein itself.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

It has now been surprisingly found, and this is an object of the invention, that a protein having the sequence shown in FIG. 3 (SEQ ID NO:3) is able to specifically bind to certain key proteins that are implicated in the activation of NF-κB. Furthermore, following binding of the protein of the invention to TNF pathway signaling molecules, the activation of NF-κB is inhibited.

It is thus an object of the invention to provide a novel protein, designated NAP, including all isoforms, variants, fragments or derivatives thereof which are capable of binding to the tumor necrosis factor receptor-associated 2 (TRAF2) protein and to one or more proteins of the signalosome (NF-κB regulatory complex). As TRAF2 is involved in the modulation or mediation of the activation of the transcription factor NF-κB, which is initiated by some of the TNF/NGF receptors, as well as others as noted above, the novel protein of the present invention by binding to TRAF2 and to signalosome proteins is therefore capable of affecting (modulating or mediating) the intracellular signaling processes initiated by various ligands (e.g. TNF, FAS ligand and others) binding to their receptors such as, for example, their modulation/mediation of NF-κB activation, via interaction directly or indirectly with TRAF proteins and/or with the signalosome or signalosome-interacting proteins.

The novel protein of the present invention is therefore a direct modulator/mediator of the intracellular biological activity of TRAF2 and signalosome (e.g. induction of NF-κB activation by TRAF2). The novel protein of the invention is likewise an indirect modulator/mediator of the intracellular biological activity of a variety of other proteins which are capable of interacting with TRAF2 directly (e.g. P75 TNF receptor) or indirectly (e.g. p55 TNF receptor) by means of their associated proteins, such as, for example, TRADD and RIP).

Another object of the invention is to provide antagonists (e.g., antibodies, peptides, organic compounds, or even some isoforms) to the above novel TRAF2-binding protein, including isoforms, analogs, fragments and derivatives thereof, which may be used to inhibit the signaling process, or, more specifically, to inhibit the activation of NF-κB and its associated involvement in cell-survival processes, when desired. Likewise, when the TRAF2-binding protein of the invention is itself inhibitory for NF-κB activation, then it is an object to provide antagonists to this TRAF2-binding protein to activate the signaling process or more specifically, to block the inhibition of NF-κB activation and hence bring about enhanced NF-κB activation, when desired.

A further object of the invention is to use the above novel TRAF2-binding protein, isoforms, analogs, fragments and derivatives thereof, to isolate and characterize additional proteins or factors, which may be involved in regulation of TRAF2/signalosome activity, e.g., other proteins which may bind to TRAF2 proteins and to signalosome proteins and influence their activity, and/or to isolate and identify other receptors or other cellular proteins further upstream or downstream in the signaling process(es) to which this novel protein, analogs, fragments and derivatives bind, and hence, in whose function they are also involved.

A still further object of the invention is to provide inhibitors which can be introduced into cells to bind or interact with the novel protein of the invention and possible isoforms thereof, which inhibitors may act to inhibit NF-κB activation, e.g., TRAF2-mediated NF-κB activation; or which may directly activate the signalosome complex, and hence, when desired, to enhance NF-κB activation.

Moreover, it is an object of the present invention to use the above-mentioned novel protein, isoforms and analogs, fragments and derivatives thereof as antigens for the preparation of polyclonal and/or monoclonal antibodies thereto. The antibodies, in turn, may be used, for example, for the purification of the new proteins from different sources, such as cell extracts or transformed cell lines.

Furthermore, these antibodies may be used for diagnostic purposes, e.g. for identifying disorders related to abnormal functioning of cellular effects mediated directly by TRAF proteins, the signalosome, or by the p55 TNF receptor, FAS/APO1 receptor, or other NF-κB inducing receptors and their associated cellular proteins (e.g., MORT-1, TRADD, RIP), which act directly or indirectly to modulate/mediate NF-κB induction, and other cellular processes, e.g., via interaction with TRAF2.

A further object of the invention is to provide pharmaceutical compositions comprising the above novel protein, isoforms, or analogs, fragments or derivatives thereof, as well as pharmaceutical compositions comprising the above noted antibodies or other antagonists.

In accordance with the present invention, a novel protein, in particular, a TRAF2- and NEMO-binding protein, has been isolated. This protein has high specificity of binding to TRAF2 and to NEMO (see Examples below) and hence is a modulator or mediator of TRAF2/NEMO intracellular activity. TRAF2 is involved in the modulation or mediation of at least one intracellular signaling pathway being the cell survival- or viability-related pathway in which TRAF-2 is directly involved in activation of NF-κB which plays a central role in cell survival. Further, TRAF2 by being capable of interacting directly or indirectly with the above noted p55 TNF receptor, p75 TNF receptor, FAS/APO1 receptors and their associated proteins MORT-1, TRADD and RIP, also is a mediator or modulator of the NF-κB induction or activation activity attributed to these receptors. TRAF2 is therefore a modulator/mediator of the cell survival pathways (as opposed to the cell death pathways) mediated by these receptors and their associated proteins and as such the extent of interaction between these receptors and/or proteins with TRAF2 and of TRAF-2 with downstream proteins leading to NF-κB induction is an important factor in the outcome of the activity of these receptors. Accordingly, NAP, plays a key role in this interaction between TRAF-2 proteins and components of the signalosome, by binding specifically to TRAF-2 and to components of the signalosome, e.g., to NEMO, and thereby modulate the activity thereof and/or have their activity modulated by interaction with TRAF2 and/or components of the signalosome.

The TRAF2/signalosome interacting protein, NAP, has been isolated and cloned using the two-hybrid system, partially and fully sequenced, and characterized, and as is detailed herein below appears to be a highly specific binding protein, and hence a specific TRAF2/NEMO modulator/mediator.

As will be used herein throughout, TRAF2 activity, is meant to include its activity in modulation/mediation of NF-κB induction/activation. Likewise, as used herein throughout, TRAF2-binding protein activity is meant to include the modulation/mediation of TRAF2 activity by virtue of specific binding to TRAF2 proteins, this modulation/mediation including modulation/mediation of cell survival pathways, in particular, those relating to NF-κB activation/induction in which TRAF2 is involved directly or indirectly and as such TRAF2-binding protein may be considered as indirect modulator/mediators of all the above mentioned proteins and possibly a number of others which are involved in cell survival, especially NF-κB activation/induction and to which TRAF2 binds, or with which TRAF2 interacts in a direct or indirect fashion.

Accordingly, the present invention provides a DNA sequence encoding NAP, or an isoform, variant, fragment or derivative of a protein capable of binding to TRAF2 and independently to a component of the signalosome.

NAP is capable of binding to TRAF2 and to NEMO.

NAP is a protein capable of binding to at least amino acids 218 to 416 of NEMO.

Other embodiments of the DNA molecule of the invention include:

(a) a cDNA of the herein designated clone 10 comprising the nucleotide sequence (SEQ ID NO:1) depicted in FIG. 1;

(b) a cDNA of the herein designated clone compl. 10 comprising the nucleotide sequence (SEQ ID NO:2) depicted in FIG. 2 or the coding region corresponding to nucleotides 497-3355 of SEQ ID NO:2;

(c) a fragment of a sequence (a) or (b) which encodes a biologically active protein capable of binding to at least amino acids 218 to 416 of NEMO;

(d) a DNA capable of hybridization to the complement of a nucleotide sequence of (a)-(c) under highly stringent conditions and which encodes a biologically active protein capable of binding to at least amino acids 218 to 416 of NEMO; and (e) a DNA whose sequence is degenerate as a result of the genetic code which encodes a biologically active protein capable of binding to at least amino acids 218 to 416 of NEMO.

Yet other embodiments of the DNA of the invention noted above include a DNA which has either the sequence contained in the herein designated cDNA clone known as clone 10, or the sequence contained in herein designated clone compl. 10, the latter encoding NAP.

Embodiments of the above DNA sequence of the invention encoding the protein NAP include:

(i) A DNA encoding the protein NAP, isoforms, fragments or analogs thereof, said NAP, isoforms, fragments or analogs thereof being capable of binding to TRAF2 and to NEMO and which is capable of modulating the activity of NF-κB;

(ii) A DNA as in (i) above, selected from the group consisting of:

a) a cDNA derived from the coding region of a native NAP protein;

b) DNA capable of hybridization to the complement of a nucleotide sequence of (a) under highly stringent conditions and which encode a biologically active NAP; and c) DNA which are degenerate as a result of the genetic code to the sequences defined in (a) and (b) and which encode a biologically active NAP protein;

(iii) A DNA as in (i) or (ii) above comprising at least part of the sequence (SEQ ID NO:2) depicted in FIG. 2 and encoding at least one active NAP protein, isoform, analog or fragment;

(iv) A DNA as in (iii) above encoding a NAP protein, isoform, analog or fragment having at least part of the amino acid sequence (SEQ ID NO:3) depicted in FIG. 3.

In another aspect, the invention provides proteins or polypeptides encoded by the above noted DNA coding sequences of the invention, the isoforms, analogs, fragments and derivatives of said proteins and polypeptides, provided that they are capable of binding to TRAF2 and/or to NEMO, preferably to at least the 222-501 amino acid sequence of TRAF2 and/or to the amino acid sequence of NEMO.

In yet another aspect, the invention provides a vector comprising any of the above DNAs according to the invention which are capable of being expressed in host cells selected from prokaryotic and eukaryotic cells; and the transformed prokaryotic and eukaryotic cells containing said vector.

The invention also provides a method for producing a protein, isoform, variant, analog, fragment or derivative encoded by any of the above DNA molecules according to the invention which comprises growing the above mentioned transformed host cells under conditions suitable for the expression of said protein, isoforms, variants analogs, fragments or derivatives, effecting post-translational modification, as necessary, for obtaining said protein, isoform, variants analogs, fragments or derivatives and isolating said expressed protein, isoforms, variants analogs, fragments or derivatives.

In a further aspect, the invention provides antibodies or active fragments or derivatives thereof, defined as molecules having the antigen-binding portion of an antibody specific for the above proteins of the invention, analogs, isoforms, fragments or derivatives thereof or specific for the NAP protein, isoform, variant, analog, fragment or derivative thereof noted above.

In a different aspect, the invention provides the following screening methods:

(i) A method for screening of a ligand capable of binding to a protein according to the invention, as noted above, including isoforms, variants, analogs, fragments or derivatives thereof, comprising contacting an affinity chromatography matrix to which said protein, isoform, variant, analog, fragment or derivative is attached with a cell extract whereby the ligand is bound to said matrix, and eluting, isolating and analyzing said ligand.

(ii) A method for screening of a DNA molecule coding for a ligand capable of binding to a protein, isoform, variant, analog, fragment or derivative according to the invention as noted above, comprising applying the yeast two-hybrid procedure in which a sequence encoding said protein, isoform, variant, analog, derivative or fragment is carried by one hybrid vector and sequences from a cDNA or genomic DNA library are carried by the second hybrid vector, transforming yeast host cells with said vectors, isolating the positively transformed cells, and extracting said second hybrid vector to obtain a sequence encoding said ligand.

Similarly, there is also provided a method for isolating and identifying proteins, isoforms, variants, analogs, fragments according to the invention noted above, capable of binding directly to TRAF2 and separately to signalosome components, comprising applying the yeast two-hybrid procedure in which a sequence encoding said TRAF2, is carried by one hybrid vector and sequence from a cDNA or genomic DNA library is carried by the second hybrid vector, the vectors then being used to transform yeast host cells and the positive transformed cells being isolated, followed by extraction of the said second hybrid vector to obtain a sequence encoding a protein which binds to said TRAF2, and retesting the so-identified clones in the same manner using the two-hybrid assay, for binding to a protein component of the signalosome, and selecting those clones that bind to both.

In yet another aspect of the invention there is provided a method for the modulation or mediation in cells of the activity of NF-κB or by other molecules to which a protein, isoform, variant, analog, fragment or derivative thereof of the invention as noted above, said method comprising treating said cells by introducing into said cells one or more of said protein, isoform, variant, analog, fragment or derivative thereof in a form suitable for intracellular introduction thereof, or introducing into said cells a DNA encoding said one or more protein, isoform, variant, analog, fragment or derivative thereof in the form of a suitable vector carrying said sequence, said vector being capable of effecting the insertion of said sequence into said cells in a way that said sequence is expressed in said cells.

Embodiments of this above method for modulation/mediation in cells of the activity of NF-κB or other molecules include:

(i) A method as above, wherein said treating of cells comprises introducing into said cells a DNA encoding said protein, isoform, fragment, analog or derivative in the form of a suitable vector carrying said DNA, said vector being capable of effecting the insertion of said DNA into said cells in a way that said DNA is expressed in said cells.

(ii) A method as above wherein said treating of said cells is by transfection of said cells with a recombinant animal virus vector comprising the steps of:

(a) constructing a recombinant animal virus vector carrying a sequence encoding a viral surface protein (ligand) that is capable of binding to a specific cell surface receptor on the surface of said cells to be treated and a second sequence encoding a protein selected from the said protein, isoforms, variants, analogs, fragments and derivatives according to the invention, that when expressed in said cells is capable of modulating/mediating the activity of NF-κB or other said molecules; and (b) infecting said cells with said vector of (a).

Likewise, the present invention also provides a method for modulating NF-κB modulated/mediated effect on cells comprising treating said cells with the molecules having the binding portion of an antibody, such as antibodies or active fragments or derivatives thereof, according to the invention as noted above, said treating being by application of a suitable composition containing said molecules to said cells, wherein when the signalosome or signalosome-interacting proteins or portions thereof of said cells are exposed on the extracellular surface, said composition is formulated for extracellular application, and when said TRAF2/signalosome and signalosome-interacting proteins are intracellular said composition is formulated for intracellular application.

Other methods of the invention for modulating the NF-κB modulated/mediated effect on cells include:

(i) A method comprising treating said cells with an antisense molecule, wherein the antisense molecule is capable of blocking the expression of the TRAF2/signalosome-interacting proteins.

(ii) A method as in (i) above wherein the antisense molecule is introduced to the cells via a recombinant virus as noted above, wherein said second sequence of said virus encodes said antisense molecule.

(iii) A method comprising applying the ribozyme procedure in which a vector encoding a ribozyme sequence capable of interacting with a cellular mRNA sequence encoding a TRAF2/signalosome-interacting protein, isoform, analog, fragment or derivative of the invention noted above, is introduced into said cells in a form that permits expression of, said ribozyme sequence in said cells, and wherein when said ribozyme sequence is expressed in said cells it interacts with said cellular mRNA sequence and cleaves said mRNA sequence resulting in the inhibition of expression of said TRAF2/signalosome-interacting protein in said cells.

It should be noted that for all the above methods of the invention, the protein of the invention as indicated, can be specifically NAP or at least one of the NAP isoforms, analogs, fragments and derivatives thereof.

In the above methods and embodiments thereof of the invention there is included also a method for the prevention or treatment of a pathological condition associated with NF-κB induction or by other molecules to which a protein, isoform, variant, analog, fragment or derivative, according to the invention, binds, said method comprising administering to a patient in need an effective amount of a protein, isoform, variant, analog, fragment or derivative, according to the invention, or a DNA molecule coding therefor, or a molecule capable of disrupting the interaction of said protein, isoform, variant, analog, fragment or derivative, with TRAF2 and/or with an signalosome protein, or any other molecule to which said protein, isoform, variant, analog, fragment or derivative binds. In this method of the invention, said protein of the invention administered to the patient in need can be specifically the protein encoded by clone 10, the protein NAP encoded by clone compl. 10, an isoform, variant, analog, derivative or fragment of NAP, or a DNA molecule coding therefor. The protein encoded by clone 10 inhibits NF-κB induction, as do other fragments of NAP.

In an additional aspect of the invention there is provided a pharmaceutical composition for the modulation of the TRAF2/signalosome and signalosome interacting protein modulated/mediated effect on cells comprising, as active ingredient an effective amount of NAP, according to the invention, its biologically active fragments, variants, analogs, derivatives or mixtures thereof.

Other pharmaceutical compositions or embodiments thereof according to the invention include:

(i) A pharmaceutical composition for modulating the TRA2F/NF-κB modulated/mediated effect on cells comprising, as active ingredient, a recombinant animal virus vector encoding a protein capable of binding a cell surface receptor and encoding NAP, or an isoform, variant, active fragment or analog thereof, according to the invention.

(ii) A pharmaceutical composition for modulating the TRAF2/NF-κB modulated/mediated effect on cells comprising as active ingredient, an antisense nucleic acid for the NAP mRNA sequence according to the invention.

A further embodiment of the above pharmaceutical composition is specifically a pharmaceutical composition for the prevention or treatment of a pathological condition associated with NF-κB induction or by other molecules to which a protein, variant, analog, isoform, fragment or derivative, according to the invention binds, said composition comprising an effective amount of a protein, variant, analog, isoform, fragment or derivative, according to the invention or a DNA molecule coding therefor, or a molecule capable of disrupting the interaction of said protein, variant, analog, isoform, fragment or derivative, with TRAF2 and/or with an signalosome protein or any other molecule to which said protein, variant, analog, isoform, fragment or derivative, binds. In a yet further specific embodiment said pharmaceutical composition comprising an effective amount of the protein encoded by clone 10, or compl. 10, of the NAP protein, an isoform, variant, variant, analog, derivative or fragment of NAP, or a DNA molecule coding therefor.

Known conditions associated with abnormal NF-κB induction include AIDS, autoimmune diseases, and tumors.

Still further aspects and embodiments of the invention are:

(i) A method for identifying and producing a ligand capable of modulating the cellular activity modulated/mediated by TRAF2/signalosome and signalosome interacting protein comprising:

a) screening for a ligand capable of binding to a polypeptide comprising at least a portion of TRAF2 and to amino acids 218 to 416 of NEMO;

b) identifying and characterizing a ligand, other than TRAF2 or NEMO, found by said screening step to be capable of said binding;

c) testing the clones identified in steps (a) and (b) for binding to NEMO and d) producing said ligand in substantially isolated and purified form.

(ii) A method for identifying and producing a ligand capable of modulating the cellular activity modulated/mediated by a protein, isoform, variant, analog, fragment or derivative, according to the invention, comprising:

a) screening for a ligand capable of binding to a polypeptide comprising at least a portion of the NAP sequence (SEQ ID NO:3) depicted in FIG. 3;

b) identifying and characterizing a ligand, other than TRAF2/NEMO, found by said screening step to be capable of said binding; and c) producing said ligand in substantially isolated and purified form.

(iii) A method for identifying and producing a ligand capable of modulating the cellular activity modulated/mediated by NAP comprising:

a) screening for a ligand capable of binding to a polypeptide comprising at least a portion of the NAP sequence (SEQ ID NO:3) depicted in FIG. 3;

b) identifying and characterizing a ligand, other than TRAF2 or NEMO, found by said screening step to be capable of said binding; and c) producing said ligand in substantially isolated and purified form.

(iv) A method for identifying and producing a ligand capable of directly or indirectly modulating the cellular activity modulated/mediated by NAP comprising:

a) screening for a molecule capable of modulating activities modulated/mediated by NAP;

b) identifying and characterizing said molecule; and c) producing said molecule in substantially isolated and purified form.

(v) A method for identifying and producing a molecule capable of directly or indirectly modulating the cellular activity modulated/mediated by a protein, isoform, variant, analog, fragment or derivative of the invention, comprising:

a) screening for a molecule capable of modulating activities modulated/mediated by a protein, isoform, variant, analog, fragment or derivative according to the invention;

b) identifying and characterizing said molecule; and c) producing said molecule in substantially isolated and purified form.

Other aspects and embodiments of the present invention are also provided as arising from the following

DETAILED DESCRIPTION OF THE INVENTION

It should be noted that, where used throughout, the following terms: "modulation/mediation of the TRAF/NF-κB complex component (or TRAF2/NEMO) effect on cells" or any other such "modulation/mediation" mentioned in the specification are understood to encompass in vitro as well as in vivo treatment and, in addition, also to encompass inhibition or enhancement/augmentation.

BRIEF DESCRIPTION OF THE DRAWINGS

FIG. 1 shows the nucleotide sequence (SEQ ID NO:1) of clone 10;

FIGS. 2A and 2B show the nucleotide sequence (SEQ ID NO:2) of clone compl. 10;

FIG. 3 shows the predicted amino acid sequence (SEQ ID NO:3) of NAP encoded by nucleotides 497-3355;

DETAILED DESCRIPTION OF THE INVENTION

For purposes of clarity and as an aid in the understanding of the invention, as disclosed and claimed herein, the following terms and abbreviations are defined below:

NF-κB complex (signalosome): within the context of this application, this term is meant to relate to the NF-κB regulatory complex, which is necessary in order to activate NF-κB. Its main components are IKAP, IKK-alpha, IKK-beta, IKK-gamma (NEMO), and optionally, NIK. The complex is reviewed in (Scheidereit, 1998), and references cited therein.

Functional isoforms, variants, analogs, derivatives and fragments: The term "functional" relates to the ability of such isoforms, derivatives and fragments to bind to a TRAF protein and to a component of the NF-κB complex. In a preferred embodiment of the invention, the TRAF protein is the TRAF2 protein and the component of the NF-κB complex is NEMO.

Biologically active: the term "biologically active" refers to the ability of a protein, isoform, analog, derivative, or fragment thereof to mediate/modulate TRAF2 or NF-κB, i.e., to modulate the effects of a TRAF protein or of the NF-κB complex.

Active: The term "active" in the context of antibody fragments or derivatives (such as single chain antibodies) relates to the ability of the fragment or derivative to retain the binding ability of the said antibody, i.e., the capability to bind to a protein or isoform, fragment, or derivative thereof capable of binding to TRAF and to a component of the NF-κB complex.

A number of methods in the art of molecular biology are not detailed herein, as they are well known to those of skill in the art. Such methods include site-directed mutagenesis, PCR cloning, phage library screening using oligonucleotide or cDNA probes, expression of cDNAs, analysis of recombinant proteins, transformation of bacterial and yeast cells, transfection of mammalian cells, and the like. Reference texts describing such methods are e.g., Sambrook et al., Molecular Cloning A Laboratory Manual, Cold Spring Harbor Laboratory; ISBN: 0879693096, 1989, Current Protocols in Molecular Biology, by F. M. Ausubel, ISBN: 047150338X, 1988, and Short Protocols in Molecular Biology, by F. M. Ausubel et al. (eds.) 3rd ed. John Wiley & Sons; ISBN: 0471137812, 1995. These publications are incorporated herein in their entirety by reference.

In order to identify TRAF2/NF-κB complex interacting proteins and potential substrates, by two hybrid screening method, the two hybrid or three-hybrid system may be used.

The two-hybrid system is used in the method of the invention essentially as described by Fields and Song (1989). Preferably, individual vectors, yeast strains, and libraries may be obtained from Clontech (Palo Alto, USA), as components of the Matchmaker two-hybrid system (#PT1265-1).

The preferred embodiment of the yeast two-hybrid system as used in the method of the invention has been described by Boldin et al., (1996). The yeast two-hybrid system has further been described in U.S. Pat. No. 5,580,736. These publications are therefore incorporated herein in their entirety by reference.

The three-hybrid system is used essentially as described by Tirode et al., (1997).

The proteins to be screened with the method of the invention are preferably provided in the form of a cDNA library. However, also genomic libraries or combinatorial libraries may also be used. The library is cloned at the C-terminal end of a transcriptional activation domain operable in yeast. Preferably, the transcriptional activation domain of the yeast Gal-4 protein is used, however, a large number of other transcriptional activators may be used. Preferably, the pGADGH vector available from Clontech (Palo Alto, Calif.) is used for cloning of the library.

The yeast strain used for screening must contain a selectable marker such as histidine synthetase, under the control of a promoter that includes a DNA sequence to which the above-mentioned DNA binding domain (transcriptional activation domain) binds specifically. Preferably, the yeast cell also contains a reporter gene under the control of a promoter that includes a DNA sequence to which the above-mentioned DNA binding domain binds specifically. The yeast strain HF7c, available from Clontech, may be used for screening with Gal-4 binding domain hybrids; the strain L40 may be used when lexA is the DNA binding domain used.

After transformation, the yeast cells are placed under selective conditions by plating onto media lacking certain amino acids, as required for the stability of the plasmids introduced thereinto.

The medium is selective for yeast cells in which the gene for the above-mentioned selection marker is activated. Preferably, the selectable marker is the histidine synthetase gene. Yeast cells expressing this gene may be selected for by culturing in medium lacking histidine. An advantage of this system is the possibility of adding the histidine synthetase inhibitor 3-aminotriazole to the growth medium. It is thus possible to inhibit growth of yeast cells in which a small amount of histidine synthetase is expressed, caused by leaking of the promoter containing the sequence to which the above-mentioned DNA binding domain specifically binds. In some clones, a weak, non-specific interaction between the TRAF and/or NF-κB complex component and the clone may cause spurious activation of the promoter. Thus, by raising the concentration of the inhibitor in the medium used for selection of interacting clones, it is possible to select only clones that interact with a certain minimal strength. The concentration of 3-aminotriazole is preferably 7.5 mM.

Clones identified by their ability to grow in medium lacking histidine are further analyzed by quantification of their reporter gene activity. Preferably, the lacZ gene is used as the reporter gene. Quantification of lacZ activity is done preferably in liquid culture, as described in Boldin et al., (1995).

In one embodiment of the invention, the above-mentioned three-hybrid system is used, wherein in a preferred embodiment thereof, TRAF2 protein is expressed in a bait vector, while the NF-κB complex component is expressed conditionally (e.g., under the control of the Met25 promoter which is positively regulated in a medium lacking methionine). In this system, clones that require the presence of both TRAF2 and NF-κB complex component for binding to TRAF2 may be detected easily by virtue of comparing the yeast growth in medium with and without methionine.

In another embodiment of the invention, the two-hybrid system is used in a two-step procedure. In a first step, clones that bind to a first bait are isolated. The first bait is preferably a TRAF protein. The so-isolated clones are then tested in a second step for binding to a signalosome component. Clones that bind to both TRAF and to the NF-κB complex (signalosome) component are selected for further study.

Clones that are able to grow in medium lacking histidine and that express lacZ activity are then selected for further study. Firstly, the proteins encoded by the clones are tested for their ability to bind nonrelevant proteins, such as Lamin. In general, Lamin-binding clones are discarded.

Clones that are found to specifically interact with TRAF2/NF-κB complex are then further analyzed. This is done with partial clones as obtained directly from the above-described screening methods, as well as with full-length clones that are obtained on the basis of the sequence of said partial clones. In order to obtain full-length clones, the sequence of the partial clone is obtained by extracting the DNA of said clone from the yeast cells by methods known to the person of skill in the art. The DNA is then transformed into bacteria in order to obtain large amounts of purified DNA, which may be used for sequencing. Sequencing is done by the chain-termination method, preferably using Sequenase2 enzyme commercially available in the sequencing kit of United States Biochemicals, Cleveland, Ohio.

The so-obtained sequence may then be entered into a database search program and overlapping sequences are identified by computer search. The programs used are well known to all of skill in the art and comprise e.g., the GCG (genetics computer group) package. Preferably, a search utility such as Basic Local Alignment Search Tool (BLAST) available from the EMBL server (e.g., http://dove.embl-heidelberg.de/Blast2/) is used. The Blastn command may be used for searching for nucleotide sequences that are overlapping or similar with the clone identified.

The protein identified by the method of the invention is provided as a fusion protein with a DNA binding domain. Therefore, the frame in which the nucleic acid sequence should be translated, is known, as it must be in-frame with the coding sequence of the DNA binding domain. The DNA sequence of the clone identified by the invention can therefore be unambiguously translated into amino acid sequence. The Blastp program, available on the above-noted EMBL server, may then be used for identification of overlapping protein sequences or similar proteins.

The TRAF2/NF-κB complex interacting protein preferably has the amino acid sequence of SEQ ID NO:3 or is a variant thereof having 85% identity, preferably 90% identity, more preferably 95% identity to SEQ ID NO:3 and being capable of binding to the NF-κB regulatory complex and to TRAF2 protein. The sequence identity can be determined using the Blastp program using the default parameters. Other common amino acid sequence alignment programs can also be suitably used because at high levels (85%, 90% and 95%) of sequence identity, the difference in alignment and calculated % sequence identity between different computer programs is negligible. It will be appreciated by those of skill in the art that the present TRAF2/NF-κB complex interacting protein also encompasses fragments of the protein having the sequence of SEQ ID NO:3 or fragments of a variant thereof, wherein the fragments of the present invention retain the capability of binding to the NF-κB regulatory complex and to TRAF2 protein.

Alternatively, or in addition to the above-noted methods of searching databases, a library, such as a genomic library or a cDNA library, may be screened in order to identify complete clones. Such screening methods are described in the above-noted Sambrook et al. (1989) and Ausubel et al. (1995). Alternatively, or in addition, PCR-based cloning techniques may be used, such as rapid amplification of cDNA ends (5' and 3' RACE, Graham et al., (1991), and references therein).

The partial clones identified in the screening assay of the invention, or the full-length clones obtained by any of the above methods, are then further investigated. This is done e.g., by testing the ability of the clones to modulate NF-κB activity and/or induction. In one embodiment, the DNA sequence of the clone is transferred to a mammalian expression vector and the so-obtained construct transfected into a cell that contains an NF-κB reactive promoter driving a reporter gene. The expression vector for expression of the clone preferably comprises a strong promoter for expression of the clone and of the second protein, such as the Rous sarcoma virus (RSV, Yamamoto et al., 1980), myeloproliferative sarcoma virus (MPSV, Artelt et al., 1988), Cytomegalovirus (CMV, Thomsen et al., 1984), or similar promoters of viral or cellular origin. Preferred NF-κB reactive promoters include the CMV promoter, the HIV promoter, and a promoter selected from the group of Immunoglobulin gene promoters. Most preferred is the HIV promoter. Preferred reporter genes include green fluorescent protein, lacZ, CAT, human growth hormone, and luciferase.

NF-κB activity may be induced in this system and the influence of the clone on the induction measured using the reporter gene. Inducers of NF-κB include TNF, overexpression of TRAF, TNF receptor or intracellular domains thereof, or the like inducers as known in the art.

The present invention relates to a DNA sequence coding for a polypeptide that interacts with TRAF2 and the signalosome proteins.

Moreover, the present invention further concerns the DNA sequences encoding a biologically active isoform, variant, fragment, functional analog, mutant or derivative of the TRAF2/NF-κB complex interacting protein, and the protein, isoform, variant, fragment, functional analog, mutant or derivative encoded thereby. The preparation of such analogs, fragments, mutants and derivatives is by standard procedure (see for example, Sambrook et al., 1989) in which in the DNA sequences encoding the TRAF2/NF-κB complex interacting protein, one or more codons may be deleted, added or substituted by another, to yield analogs having at least one amino acid residue change with respect to the native protein.

Of the above DNA sequences of the invention which encode a TRAF2/NF-κB complex interacting protein, isoform, variant, fragment, functional analog, mutant or derivative, there is also included, as an embodiment of the invention, DNA sequences capable of hybridizing with a cDNA sequence derived from the coding region of a native TRAF2/NF-κB complex interacting protein, in which such hybridization is performed under moderately stringent conditions, preferably highly stringent conditions, and which hybridizable DNA sequences encode a biologically active TRAF2/NF-κB complex interacting protein. These hybridizable DNA sequences therefore include DNA sequences which have a relatively high homology to the native TRAF2/NF-κB complex interacting protein cDNA sequence and as such represent TRAF2/NF-κB complex interacting protein-like sequences which may be, for example, naturally-derived sequences encoding the various TRAF2/NF-κB complex interacting protein isoforms, or naturally-occurring sequences encoding proteins belonging to a group of TRAF2/NF-κB complex interacting protein-like sequences encoding a protein having the activity of TRAF2/NF-κB complex interacting protein. Further, these sequences may also, for example, include non-naturally occurring, synthetically produced sequences, that are similar to the native TRAF2/NF-κB complex interacting protein cDNA sequence but incorporate a number of desired modifications. Such synthetic sequences therefore include all of the possible sequences encoding analogs, fragments and derivatives of TRAF2/NF-κB complex interacting protein, all of which have the activity of TRAF2/NF-κB complex interacting protein.

As used herein, stringency conditions are a function of the temperature used in the hybridization experiment, the molarity of the monovalent cations and the percentage of formamide in the hybridization solution. To determine the degree of stringency involved with any given set of conditions, one first uses the equation of Meinkoth et al., (1984) for determining the stability of hybrids of 100% identity expressed as melting temperature Tm of the DNA-DNA hybrid:

$$Tm = 81.5° C. + 16.6(\log M) + 0.41(\% \ GC) - 0.61 (\% \ form) - 500/L$$

where M is the molarity of monovalent cations, % GC is the percentage of G and C nucleotides in the DNA, % form is the percentage of formamide in the hybridization solution, and L is the length of the hybrid in base pairs. For each 1° C. that the Tm is reduced from the calculated for a 100% identity hybrid, the amount of mismatch permitted is increased by about 1% (Bonner et al., 1973). Thus, if the Tm used for any given hybridization experiment at the specified salt and formamide concentrations is 10° C. below the Tm calculated for a 100% hybrid according to the equation of Meikoth, hybridization will occur even if there is up to about 10% mismatch.

As used herein, "highly stringent conditions" are those which provide a Tm which is not more than 10° C. below the Tm that would exist for a perfect duplex with the target sequence, either as calculated by the above formula or as actually measured. Without limitation, examples of highly stringent (5-10° C. below the calculated or measured Tm of the hybrid) and moderately stringent (15-20° C. below the calculated or measured Tm of the hybrid) conditions use a wash solution of 2×SSC down to 0.1×SSC (standard saline citrate) and 0.5% SDS (sodium dodecyl sulfate) at the appropriate temperature below the calculated Tm of the hybrid. The ultimate stringency of the conditions is primarily due to the washing conditions, particularly if the hybridization conditions used are those which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSPE (standard saline-phosphate-EDTA)), 5×Denhardt's reagent, 0.5% SDS, 100 μg/ml denatured, fragmented salmon sperm DNA at a temperature approximately 20° to 25° C. below the Tm.

Alternatively, in addition to the high stringency of the wash conditions, hybridization can also be carried out at high stringency, such as at 65° C. in 6×SSC. The art of hybridization is set forth in Ausubel et al. (1987-2000) and more particularly in Hames et al., (1985).

To obtain the various above noted naturally occurring TRAF2/NF-κB complex interacting protein-like sequences, standard procedures of screening and isolation of naturally-derived DNA or RNA samples from various tissues may be employed using the natural TRAF2/NF-κB complex interacting protein cDNA or portion thereof as probe (see for example standard procedures set forth in Sambrook et al., 1989).

The invention relates to a TRAF2/NF-κB complex interacting protein as may be identified by the above screening assay. The invention also relates to a polypeptide or protein substantially corresponding to TRAF2/NF-κB complex interacting protein. The term "substantially corresponding" includes not only TRAF2/NF-κB complex interacting protein but also polypeptides or proteins that are analogs thereof.

Analogs that substantially correspond to TRAF2/NF-κB complex interacting protein are those polypeptides in which one or more amino acid of the TRAF2/NF-κB complex interacting protein's amino acid sequence has been replaced with another amino acid, deleted and/or inserted, provided that the resulting protein exhibits substantially the same or higher biological activity as the TRAF2/NF-κB complex interacting protein to which it corresponds.

In order to substantially correspond to TRAF2/NF-κB complex interacting protein, the changes in the sequence of TRAF2/NF-κB complex interacting proteins, such as isoforms are generally relatively minor. Although the number of changes may be more than ten, preferably there are no more than ten changes, more preferably no more than five, and most preferably no more than three such changes. While any technique can be used to find potentially biologically active proteins which substantially correspond to TRAF2/NF-κB complex interacting proteins, one such technique is the use of conventional mutagenesis techniques on the DNA encoding the protein, resulting in a few modifications. The proteins expressed by such clones can then be screened for their ability to bind to TRAF2/NF-κB complex and to modulate TRAF/NF-κB complex activity in modulation/mediation of the intracellular pathways noted above.

"Conservative" changes are those changes which would not be expected to change the activity of the protein and are usually the first to be screened as these would not be expected to substantially change the size, charge or configuration of the protein and thus would not be expected to change the biological properties thereof.

Conservative substitutions of TRAF2/NF-κB complex interacting proteins include an analog wherein at least one amino acid residue in the polypeptide has been conservatively replaced by a different amino acid. Such substitutions preferably are made in accordance with the following list as presented in Table 1A, which substitutions may be determined by routine experimentation to provide modified structural and functional properties of a synthesized polypeptide molecule while maintaining the biological activity characteristic of TRAF-2/NF-κB complex interacting protein.

TABLE 1A

| Original Residue | Exemplary Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |

TABLE 1A-continued

| Original Residue | Exemplary Substitution |
| --- | --- |
| Lys | Arg; Gln; Glu |
| Met | Leu; Tyr; Tle |
| Phe | Met; Leu; Tyr |
| Ser | Thr |
| Thr | Ser |
| Trp | Tyr |
| Tyr | Trp; Phe |
| Val | Ile; Leu |

Alternatively, another group of substitutions of TRAF2/NF-κB complex interacting protein are those in which at least one amino acid residue in the polypeptide has been removed and a different residue inserted in its place according to the following Table 1B. The types of substitutions which may be made in the polypeptide may be based on analysis of the frequencies of amino acid changes between a homologous protein of different species, such as those presented in Table 1-2 of Schulz et al., (1798), and FIGS. 3-9 of Creighton (1983). Based on such an analysis, alternative conservative substitutions are defined herein as exchanges within one of the following five groups:

TABLE 1B

| | |
| --- | --- |
| Small aliphatic, nonpolar or slightly polar residues: | Ala, Ser, Thr (Pro, Gly); |
| Polar negatively charged residues and their amides: | Asp, Asn, Glu, Gln; |
| Polar, positively charged residues: | His, Arg, Lys; |
| Large aliphatic nonpolar residues: | Met, Leu, Ile, Val (Cys); and |
| Large aromatic residues: | Phe, Tyr, Trp |

The three amino acid residues in parentheses above have special roles in protein architecture. Gly is the only residue lacking any side chain and thus imparts flexibility to the chain. This however tends to promote the formation of secondary structure other than an α-helix. Pro, because of its unusual geometry, tightly constrains the chain and generally tends to promote β-turn-like structures, although in some cases Cys can be capable of participating in disulfide bond formation which is important in protein folding. Note that Schulz at al. (1978) would merge Groups 1 and 2, above. Note also that Tyr, because of its hydrogen bonding potential, to has significant kinship with Ser, and Thr, etc.

Conservative amino acid substitutions according to the present invention, e.g., as presented above, are known in the art and would be expected to maintain biological and structural properties of the polypeptide after amino acid substitution. Most deletions and substitutions according to the present invention are those which do not produce radical changes in the characteristics of the protein or polypeptide molecule. "Characteristics" is defined in a non-inclusive manner to define both changes in secondary structure, e.g. α-helix or β-sheet, as well as changes in biological activity, e.g., binding to TRAF2/NF-κB complex and/or mediation of the effect of TRAF2/NF-κB complex on cell death.

Examples of production of amino acid substitutions in proteins which can be used for obtaining analogs of TRAF2/NF-κB complex interacting proteins for use in the present invention include any known method steps, such as presented in U.S. Pat. RE 33,653, U.S. Pat. No. 4,959,314, U.S. Pat. No. 4,588,585 and U.S. Pat. No. 4,737,462, to Mark et al.; U.S. Pat. No. 5,116,943 to Koths et al., 4,965,195 to Namen et al.; 4,879,111 to Chong et al.; and U.S. Pat. No. 5,017,691 to Lee et al.; and lysine substituted proteins presented in U.S. Pat. No. 4,904,584 (Shaw et al.).

Besides conservative substitutions discussed above which would not significantly change the activity of TRAF2/NF-κB complex interacting protein, either conservative substitutions or less conservative and more random changes, which lead to an increase in biological activity of the analogs of TRAF2/NF-κB complex interacting proteins, are intended to be within the scope of the invention.

When the exact effect of the substitution or deletion is to be confirmed, one skilled in the art will appreciate that the effect of the substitution(s), deletion(s), etc., will be evaluated by routine binding, such as co-immunoprecipitation from cells that overexpress the desired proteins and cell death assays as described in WO 97/03998, herein incorporated entirely by reference. Screening using such a standard test merely involve routine experimentation.

Acceptable TRAF2/NF-κB complex interacting analogs are those which retain at least the capability of interacting with the TRAF2/NF-κB complex, and thereby, mediate the activity of TRAF2/NF-κB complex in the intracellular pathways, or modulate the activity of TRA2F/NF-κB complex itself. In such a way, analogs can be produced which have a so-called dominant-negative effect, namely, an analog which is defective either in binding to TRAF2/NF-κB complex, or in subsequent signaling or other activity following such binding. Such analogs can be used, for example, to inhibit the NF-κB inducing effect of TRAF proteins, e.g., of TRAF-2.

At the genetic level, these analogs are generally prepared by site-directed mutagenesis of nucleotides in the DNA encoding the TRAF2/NF-κB complex interacting protein, thereby producing DNA encoding the analog, and thereafter synthesizing the DNA and expressing the polypeptide in recombinant cell culture. The analogs typically exhibit the same or increased qualitative biological activity as the naturally occurring protein (Ausubel et al., 1987-2000 and Sambrook at al., 1989).

Preparation of a TRAF2/NF-κB complex interacting protein in accordance herewith, or an alternative nucleotide sequence encoding the same polypeptide but differing from the natural sequence due to changes permitted by the known degeneracy of the genetic code, can be achieved by site-specific mutagenesis of DNA that encodes an earlier prepared analog or a native version of a TRAF2/NF-κB complex interacting protein. Site-specific mutagenesis allows the production of analogs through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 complementing nucleotides on each side of the sequence being altered. In general, the technique of site-specific mutagenesis is well known in the art, as exemplified by publications such as Adelman et al., (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., (1981), the disclosure of which is incorporated herein by reference. These phages are readily available commercially and their use is generally well known to those skilled in the art. Alternatively, plasmid vectors that contain a single-stranded phage origin of replication (Veira et al., 1987) may be employed to obtain single-stranded DNA.

In general, site-directed mutagenesis in accordance herewith is performed by first obtaining a single-stranded vector that includes within its sequence a DNA sequence that encodes the relevant polypeptide. An oligonucleotide primer bearing the desired mutated sequence is prepared synthetically by automated DNA/oligonucleotide synthesis. This primer is then annealed with the single-stranded protein-sequence-containing vector, and subjected to DNA-polymerizing enzymes such as E. coli polymerase I Klenow fragment, to complete the synthesis of the mutation-bearing strand. Thus, a mutated sequence and the second strand bears the desired mutation. This heteroduplex vector is then used to transform appropriate cells, such as E. coli JM101 cells, and clones are selected that include recombinant vectors bearing the mutated sequence arrangement.

After such a clone is selected, the nucleotide sequence encoding the mutated 2/NF-κB complex interacting protein may be removed and placed in an appropriate vector, generally a transfer or expression vector of the type that may be employed for transfection of an appropriate host.

Accordingly, a gene or nucleic acid sequence encoding for a TRAF2/NF-κB complex interacting protein can also be detected, obtained and/or modified, in vitro, in situ and/or in vivo, by the use of known DNA or RNA amplification techniques, such as PCR and chemical oligonucleotide synthesis. PCR allows for the amplification (increase in number) of specific DNA sequences by repeated DNA polymerase reactions. This reaction can be used as a replacement for cloning; all that is required is a knowledge of the nucleic acid sequence. In order to carry out PCR, primers are designed which are complementary to the sequence of interest. The primers are then generated by automated DNA synthesis. Because primers can be designed to hybridize to any part of the gene, conditions can be created such that mismatches in complementary base pairing can be tolerated. Amplification of these mismatched regions can lead to the synthesis of a mutagenized product resulting in the generation of a peptide with new properties (i.e., site directed mutagenesis). See also, e.g., Chapter 16 of Ausubel et al. (1987-2000). Also, by coupling complementary DNA (cDNA) synthesis (using reverse transcriptase) with PCR, RNA can be used as the starting material for the synthesis of the TRAF2/NF-κB complex interacting protein receptor without cloning.

Furthermore, PCR primers can be designed to incorporate new restriction sites or other features such as termination codons at the ends of the gene segment to be amplified. This placement of restriction sites at the 5' and 3' ends of the amplified nucleic acid sequence allows for gene segments encoding TRAF2/NF-κB complex interacting protein or a fragment thereof to be custom designed for ligation with other sequences and/or cloning sites in vectors.

PCR and other methods of amplification of RNA and/or DNA are well known in the art and can be used according to the present invention with only routine experimentation, based on the teaching and guidance presented herein. Known methods of DNA or RNA amplification include, but are not limited to polymerase chain reaction (PCR) and related amplification processes (see, e.g., U.S. Pat. Nos. 4,683,195, 4,683,202, 4,800,159, 4,965,188, to Mullis et al.; 4,795,699 and 4,921,794 to Tabor et al.; 5,142,033 to Innis; 5,122,464 to Wilson et al.; 5,091,310 to Innis; 5,066,584 to Gyllensten et al.; 4,889,818 to Gelfand et al.; 4,994,370 to Silver et al.; 4,766,067 to Biswas; 4,656,134 to Ringold; and Innis et al., eds., *PCR Protocols: A Guide to Method and Applications*) and RNA mediated amplification which uses anti-sense RNA to the target sequence as a template for double stranded DNA synthesis (U.S. Pat. No. 5,130,238 to Malek et al., with the tradename NASBA); and immuno-PCR which combines DNA amplification with antibody labeling (Ruzicka et al., 1993; Sano et al., 1992; and Sano et al., 1991), the entire contents of which patents and reference are entirely incorporated herein by reference.

In an analogous fashion, biologically active fragments of TRAF2/NF-κB complex interacting proteins (e.g., those of any of the TRAF2/NF-κB complex interacting proteins or its isoforms) may be prepared as noted above with respect to the analogs of TRAF2/NF-κB complex interacting protein. Suitable fragments of TRAF2/NF-κB complex interacting protein are those which retain the TRAF2/NF-κB complex interacting protein capability and which can mediate the biological activity of TRAF proteins and/or or the NF-κB complex or of other proteins associated therewith directly or indirectly. Accordingly, TRAF2/NF-κB complex interacting protein fragments can be prepared which have a dominant-negative or a dominant-positive effect as noted above with respect to the analogs. It should be noted that these fragments represent a special class of the analogs of the invention, namely, they are defined portions of TRAF2/NF-κB complex interacting proteins derived from the full TRAF2/NF-κB complex interacting protein sequence (e.g., from that of any one of the TRAF2/NF-κB complex interacting protein or its isoforms), each such portion or fragment having any of the above-noted desired activities. Such fragment may be, e.g., a peptide.

Similarly, chemical derivatives may be prepared by standard modifications of the side groups of one or more amino acid residues of the TRAF2/NF-κB complex interacting protein, its analogs or fragments, or by conjugation of the TRAF2/NF-κB complex interacting protein, its analogs or fragments, to another molecule e.g. an antibody, enzyme, receptor, etc., as are well known in the art. Accordingly, "derivatives" as used herein covers chemical derivatives which may be prepared from the functional groups which occur as side chains on the residues or the N- or C-terminal groups, by means known in the art, and are included in the invention. Derivatives may have chemical moieties such as carbohydrate or phosphate residues, provided such a fraction has the same or higher biological activity as TRAF2/NF-κB complex interacting proteins.

For example, chemical derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (for example that of seryl or threonyl residues) formed with acyl moieties.

The term "derivatives" is intended to include only those derivatives that do not change one amino acid to another of the twenty commonly occurring natural amino acids.

Expression of a protein or peptide in a mammalian cell may be done by inserting the DNA coding for the protein to be tested into a vector comprising a promoter, optionally an intron sequence and splicing donor/acceptor signals, and further optionally comprising a termination sequence. These techniques are in general described in Ausubel et al. (1987-2000).

The above promoter, intron, and termination sequences are operable in mammalian cells. The promoter is preferably a strong promoter such as the above-noted RSV, CMV, or MPSV promoter. The promoter may also be the SV40 early promoter (Everett et al., 1983, and references therein), or a cellular promoter, such as the β-actin promoter or the ELF-1 promoter (Tokushige et al., 1997). Also, a hybrid promoter may be used, such as the hybrid between the lac operator and the human ELF-1 alpha promoter as described by Edamatsu et al. (1997), the CMV-beta actin hybrid promoter described by Akagi et al., (1997), or the hybrid between the operator sequences and the CMV promoter (Furth et al., 1994, and references therein).

Intron sequences which may be inserted as complete sequences, i.e., including the splice donor and acceptor sites, may be inserted into the coding sequence of the protein which it is desired to express. Insertion if such intron sequences may enhance RNA stability and thus enhance production of the desired protein. While in principle, suitable intron sequences may be selected from any gene containing introns, preferred intron sequences are the beta-actin intron, the SV 40 intron, and the p55 TNF receptor intron.

The intron sequence may contain enhancer elements which may enhance transcription from the above-noted promoters.

Often, intron sequences also contain transcriptional or translational control sequences that confer tissue specific expression. Therefore, when it is desired to express a protein of the invention in a tissue-specific manner, such intron sequences may be advantageously employed. An example of an intron containing tissue-specific enhancer elements is the erythroid-specific enhancer located in intron 8 of the human 5-aminolevulinate synthase 2 gene (Surinya et al., 1998), and a discussion of the principle of enhancing protein production using intron sequences, together with example intron sequences, is provided in Huang et al., (1990).

Transcriptional termination sequences and polyadenylation signals may be added at the 3' end of the DNA coding for the protein that it is desired to express. Such sequences may be found in many or even most genes. Advantageously, the SV 40 polyadenylation signal is used (Schek et al., 1992, and references therein).

A preferred vector for expression of a protein in a mammalian cell is the pcDNAHis vector (Invitrogen Carlbad, Calif.) which contains the CMV promoter for driving expression of the gene encoding the desired protein. Other vectors that may be used include the pcDNA3 or pMPSVEH vectors. These vectors contain the CMV and the MPSV promoters, respectively.

Using recombinant expression of the protein to be tested, the protein can now be evaluated for its effect on the NF-κB modulating signals which are mediated e.g., by TRAF proteins. To that end, NF-κB may be induced in a variety of ways as known in the art, e.g., by treatment with TNF or IL-1 in cells responsive to such treatment by NF-κB modulation. This may also be achieved by overexpression of an NF-κB inducing proteins, e.g., the CD120a intracellular domain, the CD95 intracellular domain, or the like proteins. Receptor activation may either be achieved by contacting the receptors with ligand or by cross-linking receptors with antibodies, preferably polyclonal antibodies (see Engelmann et al., 1990).

The mammalian cells are preferably HeLa or human embryonic kidney (HEK) 293-T cells. The transfection is preferably done by the calcium phosphate method as described in Ausubel et al. (1987-2000). The morphology of the cells if evaluated one to 150 hours after transfection, preferably 4 to 35 hours and most preferably 20 hours after transfection.

Protein Purification and Generation of Antibodies

Polyclonal antibodies may be generated in rabbits, chicken, mice, rats, sheep, or similar mammals. For generation of antibodies against a protein or peptide of the invention, the protein or peptide is produced, as described above, by recombinant DNA technology in mammalian cells. The protein may also be produced in bacterial or insect cells as detailed in Chapter 16 of Ausubel et al. (1987-2000).

The protein or peptide is purified from the cells in which it has been produced. Protein purification methods are known to the person of skill in the art and are detailed, e.g., Chapter 16 of Ausubel et al. (1987-2000) and Chapters 5 and 6 of Coligan et al., (1994-1999). Advantageously, the protein may be produced as a fusion with a second protein, such as glutathione-S-transferase or the like, or a sequence tag, such as the histidine tag sequence. The use of fusion or tagged proteins simplifies the purification procedure, as described in Ausubel et al. (1987-2000) and in the instructions for the commercially available (Qiagen, GmbH 40724, Hilden, Germany) his-tag protein expression and purification kit.

If the protein or peptide has been expressed as a fusion protein, it is desirable to cleave the fusion partner before using the protein for the generation of antibodies, in order to avoid generation of antibodies against the fusion partner. The cleavage of fusion partners and the isolation of the desired protein is described in Chapter 16 of Ausubel et al (1987-2000). Vectors, protocols and reagents for expressing and purifying maltose-binding protein fused recombinant proteins are also available commercially.

When producing a peptide of the invention, it may be desirable not to remove the fusion partner, as the fusion protein may stimulate the production of antibodies against the peptide. Generally this consideration will be relevant when generating antibodies from peptides that are less than 50 amino acids in length.

As noted further above, peptide may also be synthesized by chemical methods known in the art of chemistry.

The generation of polyclonal antibodies against proteins is described in Chapter 2 of Coligan et al., (1994-1999). The generation of antibodies against peptides may necessitate some changes in protocol, because of the generally lower antigenicity of peptides when compared to proteins. The generation of polyclonal antibodies against peptides is described in Chapter 9 of Coligan et al. (1994-1999).

Monoclonal antibodies may be prepared from B cells taken from the spleen or lymphnodes of immunized animals, in particular rats or mice, by fusion with immortalized B cells under conditions which favor the growth of hybrid cells. For fusion of murine B cells, the cell line Ag-8 is preferred.

The technique of generating monoclonal antibodies is well-known in the art and described in many articles and textbooks, such as the above-noted Chapter 2 of Coligan et al. Chapter 9 therein describes the immunization, with peptides, or animals. Spleen or lymphnode cells of these animals may be used in the same way as spleen or lymphnode cells of protein-immunized animals, for the generation of monoclonal antibodies as described in Chapter 2 therein. The techniques used in generating monoclonal antibodies are further described in Kohler and Milstein, and in U.S. Pat. No. 4,376,110.

The preparation of antibodies from a gene bank of human antibodies in which the hypervariable regions thereof are replaced by almost random sequences, is described in U.S. Pat. No. 5,840,479. Such antibodies are preferred if it is difficult to immunize an animal with a given peptide or protein. Some structures are poorly immunogenic and may remain so despite of the addition of adjuvants and of linking to other proteins in fusion constructs. The antibodies described in U.S. Pat. No. 5,840,479 are further preferred if it is desired to use antibodies with a structure similar to human antibodies, for instance, when antibodies are desired that have a low immunogenicity in humans.

Once a suitable antibody has been identified, it may be desired to change the properties thereof. For instance, a chimeric antibody may achieve higher yields in production. Chimeric antibodies, wherein the constant regions are replaced with constant regions of human antibodies, are further desired when antibodies of low immunogenicity in humans are sought. The generation of chimeric antibodies is described in a number of publications, such as Cabilly et al., 1984; Morrison et al., 1984; Boulianne et al, 1984; EP 125023, EP 171496, EP 173494, EP 184187, WO 86/01533, WO 87/02671, and Harlow et al., 1988).

Another type of antibody is an anti-idiotypic antibody. An anti-idiotypic (anti-Id) antibody is an antibody which recognizes unique determinants generally associated with the antigen-binding site of an antibody. An idiotypic (Id) antibody can be prepared by immunizing an animal of the same species and genetic type (e.g., mouse strain) as the source of the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against the TRAF/NF-κB complex interacting protein, analogs, fragments or derivatives thereof, of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an epitope of the above TRAF/NF-κB complex interacting protein, or analogs, fragments and derivatives thereof. The anti-Id mAbs thus have their own idiotypic epitopes, or "idiotopes" structurally similar to the epitope being evaluated.

The term "molecule which includes the antigen-binding portion of an antibody" is intended to include not only intact immunoglobulin/antibody molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, and chimeric or single-chain antibodies incorporating such reactive fraction. Fab and F(ab')$_2$ fragments lack the Fc fragment of intact antibody, clear more rapidly from the circulation, and may have less non-specific tissue binding than an intact antibody (Wahl et al., 1983).

It will be appreciated that Fab and F(ab')$_2$ and other fragments of the antibodies useful in the present invention may be used for the detection and quantitation of the TRAF/NF-κB complex interacting protein according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

Immunoassays

The antibodies, including fragments of antibodies, according to the present invention in the present invention may be used to quantitatively or qualitatively detect the TRAF2/NF-κB complex interacting protein in a sample or to detect the presence of cells which express the TRAF2/NF-κB complex interacting protein of the present invention. This can be accomplished by immunofluorescence techniques employing a fluorescently labeled antibody (see below) coupled with light microscopic, flow cytometric, or fluorometric detection.

The antibodies (or fragments thereof) useful in the present invention may be employed histologically, as in immunofluorescence or immunoelectron microscopy, for in situ detection of the TRAF2/NF-κB complex interacting protein of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the TRAF2/NF-κB complex interacting protein, but also its distribution on the examined tissue. Using the present invention, those of ordinary skill will readily perceive that any of wide variety of histological methods (such as staining procedures) can be modified in order to achieve such in situ detection.

Such assays for the TRAF2/NF-κB complex interacting protein of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying the TRAF2/NF-κB complex interacting protein, and detecting the antibody by any of a number of techniques well known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know many other suitable carriers for binding antibody or antigen, or will be able to ascertain the same by use of routine experimentation.

The binding activity of a given lot of antibody, of the invention as noted above, may be determined according to well known methods. Those skilled in the art will be able to determine operative and optimal assay conditions for each determination by employing routine experimentation. Other such steps as washing, stirring, shaking, filtering and the like may be added to the assays as is customary or necessary for the particular situation.

One of the ways in which an antibody in accordance with the present invention can be detectably labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactive labeling the antibodies or antibody fragments, it is possible to detect R-PTPase through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a geiger counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectably labeled using fluorescence emitting metals such as $^{152}$E, or others of the lanthanide series. These metals can be attached to the antibody using such metal chelating groups such as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

The creation of immunoassays, such as RIA or ELISA, has been described in many articles, textbooks, and other publications. Reference is made to WO 97/03998, p. 48, line 4 to p.

52, line 27. Immunoassays of the invention may be of two general types: Firstly, immunoassays using immobilized TRAF2/NF-κB complex interacting protein, or an equivalent peptide, may be used in the quantification of caspase-8. Secondly, immunoassays using immobilized antibodies directed against an epitope of a TRAF2/NF-κB complex interacting protein may be used to quantify TRAF2/NF-κB complex interacting proteins.

Such assays may find use in diagnostics, as the level of caspase-8 and of other proteins involved in apoptotic pathways may need to be evaluated in a number of disorders or syndromes where involvement of such pathways is a possibility.

Antisense

The clones obtained in the screening of the invention are expected to be partial clones. Complete clones were obtained as described above and is exemplified further below. The DNA sequence of a complete clone and of the partial clone initially found in the screening of the invention may find a variety of uses.

For example, in order to manipulate the expression of a TRAF2/NF-κB complex interacting protein, it may be desirable to produce antisense RNA in a cell. To this end, the complete or partial cDNA coding for the TRAF2/NF-κB complex-interacting protein is inserted into an expression vector comprising a promoter, as noted further above. The 3' end of the cDNA is thereby inserted adjacent to the 3' end of the promoter, with the 5' end of the cDNA being separated from the 3' end of the promoter by said cDNA. Upon expression of the cDNA in a cell, an antisense RNA is therefore produced which is incapable of coding for the protein. The presence of antisense RNA in the cell reduces the expression of the cellular (genomic) copy of the TRAF2/NF-κB complex interacting protein gene.

For the production of antisense RNA, the complete cDNA may be used. Alternatively, a fragment thereof may be used, which is preferably between about 9 and 2,000 nucleotides in length, more preferably between 15 and 500 nucleotides, and most preferably between 30 and 150 nucleotides.

The fragment is preferably corresponding to a region within the 5' half of the cDNA, more preferably the 5' region comprising the 5' untranslated region and/or the first exon region, and most preferably comprising the ATG translation start site. Alternatively, the fragment may correspond to DNA sequence of the 5' untranslated region only.

A synthetic oligonucleotide may be used as antisense oligonucleotide. The oligonucleotide is preferably a DNA oligonucleotide. The length of the antisense oligonucleotide is preferably between 9 and 150, more preferably between 12 and 60, and most preferably between 15 and 50 nucleotides. Suitable antisense oligonucleotides that inhibit the production of the protein of the present invention from its encoding mRNA can be readily determined with only routine experimentation through the use of a series of overlapping oligonucleotides similar to "gene walking" technique that is well-known in the art. Such a "walking" technique as well-known in the art of antisense development can be done with synthetic oligonucleotides to walk along the entire length of the sequence complementary to the mRNA in segments on the order of 9 to 150 nucleotides in length. This "gene walking" technique will identify the oligonucleotides that are complementary to accessible regions on the target mRNA and exert inhibitory antisense activity.

Alternatively, an oligonucleotide based on the coding sequence of a protein capable of binding to NF-κB regulatory complex and to TRAF2 can be designed using Oligo 4.0 (National Biosciences, Inc.). Antisense molecules may is also be designed to inhibit translation of an mRNA into a polypeptide by preparing an antisense which will bind in the region spanning approximately −10 to +10 nucleotides at the 5' end of the coding sequence.

The mechanism of action of antisense RNA and the current state of the art on use of antisense tools is reviewed in Kumar et al., (1998). The use of antisense oligonucleotides in inhibition of BMP receptor synthesis has been described by Yeh et al., (1998). The use of antisense oligonucleotides for inhibiting the synthesis of the voltage-dependent potassium channel gene Kv1.4 has been described by Meiri et al., (1998). The use of antisense oligonucleotides for inhibition of the synthesis of Bcl-x has been described by Kondo et al., (1998). The therapeutic use of antisense drugs is discussed by Stix (1998); Flanagan, (1998); Guinot et al., (1998), and references therein.

Modifications of oligonucleotides that enhance desired properties are generally used when designing antisense oligonucleotides. For instance, phosphorothioate bonds are used instead of the phosphoester bonds that naturally occur in DNA, mainly because such phosphorothioate oligonucleotides are less prone to degradation by cellular enzymes. Peng et al. teach that undesired in vivo side effects of phosphorothioate oligonucleotides may be reduced when using a mixed phosphodiester-phosphorothioate backbone. Preferably, 2'-methoxyribonucleotide modifications in 60% of the oligonucleotide is used. Such modified oligonucleotides are capable of eliciting an antisense effect comparable to the effect observed with phosphorothioate oligonucleotides. Peng et al. teach further that oligonucleotide analogs incapable of supporting ribonuclease H activity are inactive.

Therefore, the preferred antisense oligonucleotide of the invention has a mixed phosphodiester-phosphorothioate backbone. Preferably, 2'-methoxyribonucleotide modifications in about 30% to 80%, more preferably about 60%, of the oligonucleotide are used.

In the practice of the invention, antisense oligonucleotides or antisense RNA may be used. The length of the antisense RNA is preferably from about 9 to about 3,00 nucleotides, more preferably from about 20 to about 1,000 nucleotides, most preferably from about 50 to about 500 nucleotides.

In order to be effective, the antisense oligonucleotides of the invention must travel across cell membranes. In general, antisense oligonucleotides have the ability to cross cell membranes, apparently by uptake via specific receptors. As the antisense oligonucleotides are single-stranded molecules, they are to a degree hydrophobic, which enhances passive diffusion through membranes. Modifications may be introduced to an antisense oligonucleotide to improve its ability to cross membranes. For instance, the oligonucleotide molecule may be linked to a group which includes partially unsaturated aliphatic hydrocarbon chain and one or more polar or charged groups such as carboxylic acid groups, ester groups, and alcohol groups. Alternatively, oligonucleotides may be linked to peptide structures, which are preferably membranotropic peptides. Such modified oligonucleotides penetrate membranes more easily, which is critical for their function and may therefore significantly enhance their activity. Palmityl-linked oligonucleotides have been described by Gerster et al., (1998). Geraniol-linked oligonucleotides have been described by Shoji et al., (1998). Oligonucleotides linked to peptides, e.g., membranotropic peptides, and their preparation have been described by Soukchareun et al., (1998). Modifications of antisense molecules or other drugs that target the molecule to certain cells and enhance uptake of the oligonucleotide by said cells are described by Wang, (1998).

The antisense oligonucleotides of the invention are generally provided in the form of pharmaceutical compositions. These compositions are for use by injection, topical administration, or oral uptake.

Preferred uses of the pharmaceutical compositions of the invention by injection are subcutaneous injection, intraperitoneal injection, and intramuscular injection.

The pharmaceutical composition of the invention generally comprises a buffering agent, an agent which adjusts the osmolarity thereof, and optionally, one or more carriers, excipients and/or additives as known in the art, e.g., for the purposes of adding flavors, colors, lubrication, or the like to the pharmaceutical composition.

Carriers may include starch and derivatives thereof, cellulose and derivatives thereof, e.g., microcrystalline cellulose, Xanthum gum, and the like. Lubricants may include hydrogenated castor oil and the like.

A preferred buffering agent is phosphate-buffered saline solution (PBS), which solution is also adjusted for osmolarity.

A preferred pharmaceutical formulation is one lacking a carrier. Such formulations are preferably used for administration by injection, including intravenous injection.

The preparation of pharmaceutical compositions is well known in the art and has been described in many articles and textbooks, see e.g., Remington's Pharmaceutical Sciences, Gennaro A. R. ed., Mack Publishing Company, Easton, Pa., 1990, and especially p 1521-1712 therein.

Additives may also be selected to enhance uptake of the antisense oligonucleotide across cell membranes. Such agents are generally agents that will enhance cellular uptake of double-stranded DNA molecules. For instance, certain lipid molecules have been developed for this purpose, including the transfection reagents DOTAP (Boehringer Mannheim), Lipofectin, Lipofectam, and Transfectam, which are available commercially. For a comparison of various of these reagents in enhancing antisense oligonucleotide uptake, see e.g., Quattrone et al., (1995) and Capaccioli et al., (1993). The antisense oligonucleotide of the invention may also be enclosed within liposomes. The preparation and use of liposomes, e.g., using the above-mentioned transfection reagents, is well-known in the art. Other methods of obtaining liposomes include the use of Sendai virus or of other viruses. Examples of publications disclosing oligonucleotide transfer into cells using the liposome technique are, e.g., Meyer et al., (1998); Kita et al., (1999); Nakamura et al., (1998); Abe et al., (1998); Soni et al., (1998); Bai et al., (1998), see also discussion in the same Journal p. 819-20, Bochot et al., (1998); Noguchi at al., (1998); Yang et al., (1998); Kanamaru et al., (1998), and references therein. The use of Lipofectin in liposome-mediated oligonucleotide uptake is described in Sugawa et al., (1998). The use of fusogenic cationic-lipid-reconstituted influenza-virus envelopes (cationic virosomes) is described in Waelti et al., (1998).

The above-mentioned cationic or nonionic lipid agents not only serve to enhance uptake of oligonucleotides into cells, but also improve the stability of oligonucleotides that have been taken up by the cell.

Ribozymes

Given the known mRNA sequence of a gene, ribozymes, which are RNA molecule that specifically bind and cleave said mRNA sequence (see e.g., Chen et al., (1992); Zhao et al., (1993); Shore et al., (1993); Joseph et al., (1993); Shimayama et al., (1993); and Cantor et al., (1993), may be designed.

Accordingly, a ribozyme-encoding RNA sequence may be designed that cleaves the mRNA of a TRAF/NF-κB complex interacting protein of the present invention. The site of cleavage is preferably located in the coding region or in the 5' nontranslated region, more preferably, in the 5' part of the coding region close to the AUG translational start codon.

A DNA encoding a ribozyme according to the present invention may be introduced into cells by way of DNA uptake, is uptake of modified DNA (see modifications for oligonucleotides and proteins that result in enhanced membrane permeability, as described above for oligonucleotides and described below for proteins), or viral vector-mediated gene transfer.

Introduction of TRAF2/NF-κB Complex Interacting Proteins, Peptides, and DNA into Cells The present invention provides TRAF2/NF-κB complex interacting proteins, peptides derived therefrom, antisense DNA molecules, and oligonucleotides. A therapeutic or research-associated use of these tools necessitates their introduction into cells of a living organism or into cultured cells. For this purpose, it is desired to improve membrane permeability of peptides, proteins and oligonucleotides. Ways to improve membrane permeability of oligonucleotides have been discussed above. The same principle, namely, derivatization with lipophilic structures, may also be used in creating peptides and proteins with enhanced membrane permeability. For instance, the sequence of a known membranotropic peptide as noted above may be added to the sequence of the peptide or protein. Further, the peptide or protein may be derivatized by partly lipophilic structures such as the above-noted hydrocarbon chains, which are substituted with at least one polar or charged group. For example, lauroyl derivatives of peptides have been described by Muranishi et al., (1991). Further modifications of peptides and proteins include the oxidation of methionine residues to thereby create sulfoxide groups, as described by Zacharia et al., (1991). Zacharia and coworkers also described peptide or derivatives wherein the relatively hydrophobic peptide bond is replaced by its ketomethylene isoester ($COCH_2$). It is known to those of skill in the art of protein and peptide chemistry these and other modifications enhance membrane permeability.

Another way of enhancing membrane permeability is to make use of receptors, such as virus receptors, on cell surfaces in order to induce cellular uptake of the peptide or protein. This mechanism is used frequently by viruses, which bind specifically to certain cell surface molecules. Upon binding, the cell takes the virus up into its interior. The cell surface molecule is called a virus receptor. For instance, the integrin molecules CAR and AdV have been described as virus receptors for Adenovirus (Hemmi et al., 1998, and references cited therein). The CD4, GPR1, GPR15, and STRL33 molecules have been identified as receptors/coreceptors for HIV (Edinger et al., 1998 and references cited therein).

By conjugating peptides, proteins or oligonucleotides to molecules that are known to bind to cell surface receptors, the membrane permeability of said peptides, proteins or oligonucleotides will be enhanced. Examples of suitable groups for forming conjugates are sugars, vitamins, hormones, cytokines, transferrin, asialoglycoprotein, and the like molecules. Low et al., U.S. Pat. No. 5,108,921, describes the use of these molecules for the purpose of enhancing membrane permeability of peptides, proteins and oligonucleotides, and the preparation of said conjugates.

Low and coworkers further teach that molecules such as folate or biotin may be used to target the conjugate to a multitude of cells in an organism, because of the abundant and nonspecific expression of the receptors for these molecules.

The above use of cell surface proteins for enhancing membrane permeability of a peptide, protein or oligonucleotide of the invention may also be used in targeting the peptide, protein or oligonucleotide of the present invention to certain cell types or tissues. For instance, if it is desired to target cancer cells, it is preferable to use a cell surface protein that is expressed more abundantly on the surface of those cells. Examples include the folate receptor, the mucin antigens MUC1, MUC2, MUC3, MUC4, MUC5AC, MUC5B, and MUC7, the glycoprotein antigens KSA, carcinoembryonic antigen, prostate-specific membrane antigen (PSMA), HER-2/neu, and human chorionic gonadotropin-beta. The above-noted Wang et al., 1998, teaches the use of folate to target cancer cells, and Zhang et al., (1998), teaches the relative abundance of each of the other antigens noted above in various types of cancer and in normal cells.

The protein, peptide or oligonucleotide of the invention may therefore, using the above-described conjugation techniques, be targeted to a certain cell type. For instance, if it is desired to enhance NF-κB induction in cells of the lymphocytic lineage, a NF-κB complex positive modulating protein or peptide of the invention may be targeted at such cells, for instance, by using the MHC class II molecules that are expressed on these cells, or by using the IL-2 receptor marker which preferably appears on the surface of activated cells. The skilled person will recognize the possibilities of using a cell surface marker selected from a multitude of known markers of lymphoid and other cells, depending on the cell type to be targeted, and of these, further selecting those that are expressed constitutively or inducibly. For instance, if it is desired to reduce NF-κB induction in the context of an autoimmune disease, it may be advantageous, according to the invention, to use a cell surface marker that is induced when lymphoid cells are activated. Specific markers that are activated in the context of the specific autoimmune disease to be treated are preferred. For instance, in rheumatoid arthritis, the expression of cell surface markers ICAM-1, PECAM-1 and E selectin is up-regulated in rheumatic nodules and/or nearby blood vessels, while the T cell marker, CD30, appears to be up-regulated in T cells involved in the disease process (see e.g., Elewaut et al., (1998).

This may be achieved by coupling an antibody, or the antigen-binding site thereof, directed against the constant region of said MHC class II molecule or against another desired cell surface marker as mentioned above, to the protein or peptide of the invention. Furthermore, numerous cell surface receptors for various cytokines and other cell communication molecules have been described, and many of these molecules are expressed in more or less tissue- or cell-type restricted fashion. Thus, when it is desired to target a subgroup of T cells, the CD4 T cell surface molecule may be used for producing the conjugate of the invention. CD4-binding molecules are provided by the HIV virus, whose surface antigen gp42 is capable of specifically binding to the CD4 molecule. A TRAF2/NF-κB complex downmodulating protein or peptide of the present invention may be advantageously targeted to T cells in treating patients who suffer from autoimmune reactions based upon T cells, such as patients with lupus erythematosis. An example of a suitable protein according to the invention would be the protein encoded by clone 10, or derivatives, isoforms or fragments thereof with about the same biological activity.

Virus-Mediated Cellular Targeting

The proteins, peptides and antisense sequences of the present invention may be introduced into cells by the use of a viral vector. The use of a vaccinia vector for this purpose is described in Chapter 16 of Ausubel et al. (1987-2000). The use of adenovirus vectors has been described e.g. by Teoh et al., (1998); Narumi et al., (1998); Pederson et al., (1998), Guang-Lin et al., (1998), and references therein, Nishida et al., (1998); Schwarzenberger et al., (1998), and Cao et al., (1998). Retroviral transfer of antisense sequences has been described by Daniel et al., (1998). The use of SV-40 derived viral vectors and SV-40 based packaging systems has been described by Fang et al., (1997). The use of papoviruses which specifically target B-lymphocytes, has been described by Langner et al., (1998).

When using viruses as vectors, the viral surface proteins are generally used to target the virus. As many viruses, such as the above adenovirus, are rather unspecific in their cellular tropism, it may be desirable to impart further specificity by using a cell-type or tissue-specific promoter. Griscelli et al., (1998) teach the use of the ventricle-specific cardiac myosin light chain 2 promoter for heart-specific targeting of a gene whose transfer is mediated by adenovirus.

Alternatively, the viral vector may be engineered to express an additional protein on its surface, or the surface protein of the viral vector may be changed to incorporate a desired peptide sequence. The viral vector may thus be engineered to express one or more additional epitopes which may be used to target said viral vector. For instance, cytokine epitopes, MHC class II-binding peptides, or epitopes derived from homing molecules may be used to target the viral vector in accordance with the teaching of the invention. The above Langer et al. (1998) reference teach the use of heterologous binding motifs to target B-lymphotrophic papoaviruses.

Pharmaceutical Compositions

The pharmaceutical compositions of the invention are prepared generally as known in the art. Thus, pharmaceutical compositions comprising nucleic acids, e.g., ribozymes, antisense RNA or antisense oligonucleotides, are prepared as described above for pharmaceutical compositions comprising oligonucleotides and/or antisense RNA. The above consideration apply generally also to other pharmaceutical compositions. For instance, the pharmaceutical composition of the invention may contain naked DNA, e.g., DNA encoding the NAP protein or isoforms, fragments or derivatives thereof and pharmaceutically acceptable carrier as known in the art. A variety of ways to enhance uptake of naked DNA is known in the art. For instance, cationic liposomes (Yotsuyanagi et al., 1998), dicationic amphiphiles (Weissig et al., 1998), fusogenic liposomes, (Mizuguchi et al., 1996), mixtures of stearyl-poly(L-lysine) and low density lipoprotein (LDL), (terplex, Kim et al., 1998), and even whole bacteria of an attenuated mutant strain of *Salmonella Typhimurium* (Paglia et al., 1998) have been used in the preparation of pharmaceutical compositions containing DNA.

Administration of virus particles has been described in prior art publications, see e.g., U.S. Pat. No. 5,882,877, where Adenovirus based vectors and administration of the DNA thereof is described. The viral DNA was purified on a CsCl gradient and then dialyzed against Tris-buffered saline to remove CsCl. In these preparations, viral titers (pfu/ml) of $10^{14}$ to $10^{10}$ are preferably used. Administration of virus particles as a solution in buffered saline, to be preferably administered by subcutaneous injection, is known from U.S. Pat. No. 5,846,546. Croyle and coworkers describe a process for the preparation of a pharmaceutical composition of recombinant adenoviral vectors for oral gene delivery, using CsCl gradients and lyophilization in a sucrose-containing buffer (Pharm. Dev. Technol. 3, 365-72, 1998).

Where the pharmaceutical composition of the invention includes a peptide or protein according to the present invention, the composition will generally contain salts, preferably in physiological concentration, such as PBS (phosphate-buffered saline), or sodium chloride (0.9% w/v), and a buffering agent, such as phosphate buffer in water or in the well-known PBS buffer. In the following section, the term "peptide" is meant to include all proteins or peptides according to the invention. The preparation of pharmaceutical compositions is well known in the art, see e.g., U.S. Pat. Nos. 5,736,519, 5,733,877, 5,554,378, 5,439,688, 5,418,219, 5,354,900, 5,298,246, 5,164,372, 4,900,549, 4,755,383, 4,639,435, 4,457,917, and 4,064,236.

The peptide of the present invention, or a pharmacologically acceptable salt thereof is preferably mixed with an excipient, carrier, diluent, and optionally, a preservative or the like, pharmacologically acceptable to vehicles as known in the art, see e.g., the above U.S. patents. Examples of excipients include, glucose, mannitol, inositol, sucrose, lactose, fructose, starch, corn starch, microcrystalline cellulose, hydroxypropylcellulose, hydroxypropyl-methylcellulose, polyvinylpyrrolidone and the like. Optionally, a thickener may be added, such as a natural gum, a cellulose derivative, an acrylic or vinyl polymer, or the like.

The pharmaceutical composition is provided in solid, liquid or semi-solid form. A solid preparation may be prepared by blending the above components to provide a powdery composition. Alternatively, the pharmaceutical composition is provided as a lyophilized preparation. The liquid preparation is provided preferably as an aqueous solution, aqueous suspension, oil suspension or microcapsule composition. A semi-solid composition is provided preferably as hydrous or oily gel or ointment. About 0.001 to 60 w/v %, preferably about 0.05 to 25 w/v % of peptide is provided in the composition.

A solid composition may be prepared by mixing an excipient with a solution of the peptide of the invention, gradually adding a small quantity of water, and kneading the mixture. After drying, preferably in vacuo, the mixture is pulverized. A liquid composition may be prepared by dissolving, suspending or emulsifying the peptide of the invention in water, a buffer solution or the like. An oil suspension may be prepared by suspending or emulsifying the peptide of the invention or protein in an oleaginous base, such as sesame oil, olive oil, corn oil, soybean oil, cottonseed oil, peanut oil, lanolin, petroleum jelly, paraffin, Isopar, silicone oil, fatty acids of 6 to 30 carbon atoms or the corresponding glycerol or alcohol esters. Buffers include Sorensen buffer (Ergeb. Physiol., 12, 393 1912), Clark-Lubs buffer (J. Bact., 2, (1), 109 and 191, 1917), Macllvaine buffer (J. Biol. Chem., 49, 183, 1921), Michaelis buffer (Die Wasserstoffinonenkonzentration, p. 186, 1914), and Kolthoff buffer (Biochem. Z., 179, 410, 1926).

A composition may be prepared as a hydrous gel, e.g. for transnasal administration. A hydrous gel base is dissolved or dispersed in aqueous solution containing a buffer, and the peptide of the invention, and the solution warmed or cooled to give a stable gel.

Preferably, the peptide of the invention is administered through intravenous, intramuscular or subcutaneous administration. Oral administration is expected to be less effective, because the peptide may be digested before being taken up. Of course, this consideration may apply less to a peptide of the invention which is modified, e.g., by being a cyclic peptide, by containing non-naturally occurring amino acids, such as D-amino acids, or other modifications which enhance the resistance of the peptide to biodegradation. Decomposition in the digestive tract may be lessened by use of certain compositions, for instance, by confining the peptide of the invention in microcapsules such as liposomes. The pharmaceutical composition of the invention may also be administered to other mucous membranes. The pharmaceutical composition is then provided in the form of a suppository, nasal spray or sublingual tablet. The dosage of the peptide of the invention may depend upon the condition to be treated, the patient's age, bodyweight, and the route of administration, and will be determined by the attending physician.

The uptake of a peptide of the invention may be facilitated by a number of methods. For instance, a non-toxic derivative of the cholera toxin B subunit, or of the structurally related subunit B of the heal-labile enterotoxin of enterotoxic *Eschericia coli* may be added to the composition, see U.S. Pat. No. 5,554,378.

In another embodiment, the peptide of the invention is provided in a pharmaceutical composition comprising a biodegradable polymer selected from poly-1,4-butylene succinate, poly-2,3-butylene succinate, poly-1,4-butylene fumarate and poly-2,3-butylene succinate, incorporating the peptide of the invention as the pamoate, tannate, stearate or palmitate thereof. Such compositions are described, e.g., in U.S. Pat. No. 5,439,688.

In another embodiment, a composition of the invention is a fat emulsion. The fat emulsion may be prepared by adding to a fat or oil about 0.1-2.4 w/w of emulsifier such as a phospholipid, an emulsifying aid, a stabilizer, mixing mechanically, aided by heating and/or removing solvents, adding water and isotonic agent, and optionally, adjusting adding the pH agent, isotonic agent. The mixture is then homogenized. Preferably, such fat emulsions contain an electric charge adjusting agent, such as acidic phospholipids, fatty acids, bilic acids, and salts thereof. Acidic phospholipids include phosphatidylserine, phosphatidylglycerol, phosphatidylinositol, and phosphatidic acid. Bilic acids include deoxycholic acid, and taurocholic acid. The preparation of such pharmaceutical compositions is described in U.S. Pat. No. 5,733,877.

Having now generally described the invention, the same will be more readily understood through reference to the following examples which are provided by way of illustration and is not intended to be limiting of the present invention.

Example 1

Cloning

A cDNA library prepared from B-cells (Surfee et al., 1993) was screened for proteins that associate with NEMO, using the two hybrid technique as described in Boldin et al., (1996) and below. The cDNAs of this library were inserted into the XhoI site of the pACT based vector pSE1107 in fusion with the GAL4 activation domain. Yeast strain HF7c strain was used as the host strain for the purposes of transformation and screening with the two-hybrid assay. This strain carries the auxotrophic markers trp1 and leu2, and therefore cannot grow in minimal synthetic medium that lacks tryptophan and leucine, unless they also bear a plasmid carrying the wild-type versions of the genes TRP1 and LEU2. The HF7c strain also carries deletion mutations in its GAL4 and GAL80 genes (gal4-542 and ga180-538, respectively) and carries the lacZ reporter gene, fused to three copies of the GAL4 17-mer consensus sequence and the TATA portion of the CYC1 promoter in its genotype. The GA4 17-mers are responsive to the GAL4 transcriptional activator. In addition, this yeast strain also carries the HIS3 reporter gene fused to the upstream activating sequence (UAS) and the TATA portion of the GAL1 promoter. The two hybrid screen was used in order to identify factors that are associated with a particular molecule that serves as a "bait". In the present invention, NEMO, that was cloned into the vector pGBT9, served as the bait. To create, the bait for the screen, PCR-amplified complete ORF of human NEMO cDNA was introduced into pGBT9 vector linearized with SmaI. NEMO was co-expressed together with the screened B-cell cDNA library in the yeast strain HF7c. The PCR-cloned NEMO was a recombinant fusion with the GAL4 DNA-binding domain whereas the screened cDNA library was a recombinant fusion with the GAL4 activation domain in the pSE1107 vector. The HIS3 reporter gene in HF7c was fused to the upstream activating sequence (UAS) of the GAL1 promoter which is responsive to GAL4 transcriptional activator. Transformants that contained both pGBT9 and pSE1107 plasmids were selected for growth on plates without tryptophan and leucine. In a second step, positive clones, which expressed two hybrid proteins that interact with each other and therefore activated GAL1-HIS3, were picked up from plates devoid of tryptophan, leucine and histidine and containing 50 mM 3-aminotriazol (3AT). Only in transformants that expressed both NEMO and a protein capable of interacting with it would the GAL4 DNA-binding domain and the transcriptional activation domain be brought together to activate the GAL1 promoter and express the HIS3 reporter gene, which is fused to the UAS and the TATA portion of the GAL1 promoter.

The screen yielded approximately 2000 clones which were able to grow on 3AT plates lacking Trp, Leu, and His. DNA prepared from 165 randomly selected positive clones served for transient co-transfection of SFY526 yeast strain together with TRAF2 cloned into the pGBT9 vector. Assay for β-galactosidase activity was performed on the transformed SFY526 yeast colonies according to the protocol in Clontech Latboratories' manual are described in brief as follows: Transformants were allowed to grow at 30° C. for 2-4 days until reaching about 2 mm in diameter and then transferred onto Whatman filters. The filters were subjected to a freeze/thaw treatment in order to permeabilize the cells, then soaked in a buffer (16.1 mg/ml $Na_2HPO_4.7H_2O$; 5.5 mg/ml $NaH_2PO_4.H_2O$; 0.75 mg/ml KCl; 0.75 mg/ml $MgSO_4.7H_2O$, pH=7) containing 0.33 mg/ml X-gal and 0.35 mM β-mercaptoethanol. Colonies were monitored for development of blue color which is an indication for induction of β-galactosidase. Thus, the blue color that developed was an indication for yeast colonies that contain cDNA encoding a protein or polypeptide that binds to NEMO.

The results of a two hybrid specificity test carried out on one of the clones, clone 10, together with various signaling proteins, are summarized in Table 2, below. Faster binding kinetics is indicative of a stronger interaction. The proteins that bind specifically to clone 10 (RAP-2 and TRAF2) are shown in bold type in Table 2.

TABLE 2

| Gal-BD Construct | Kinetics of interaction with Gal-AD-clone 10 |
|---|---|
| Bcl-2 | >12 hrs. |
| Cyclin D | >12 hrs. |
| ICE | >12 hrs. |
| Lamin | >12 hrs. |
| MACH | >12 hrs. |
| MORT-1 | >12 hrs. |
| NIK | >12 hrs. |
| RAP-2 | 20 min. |
| RIP | >12 hrs. |
| TRADD | >12 hrs. |
| TRAF-2 | 20 min. |

TABLE 2-continued

By applying several steps of PCR amplification using cDNA clone 10, the antisense primer of SEQ ID NO:4, and a primer designed to match the 5'-arm of the cDNA library vector, the full length cDNA was cloned from cDNA libraries obtained from RNA of human tissues. This cDNA clone was designated clone compl. 10 (complete clone 10).

Example 2

Sequencing New Clones

Figure 1:
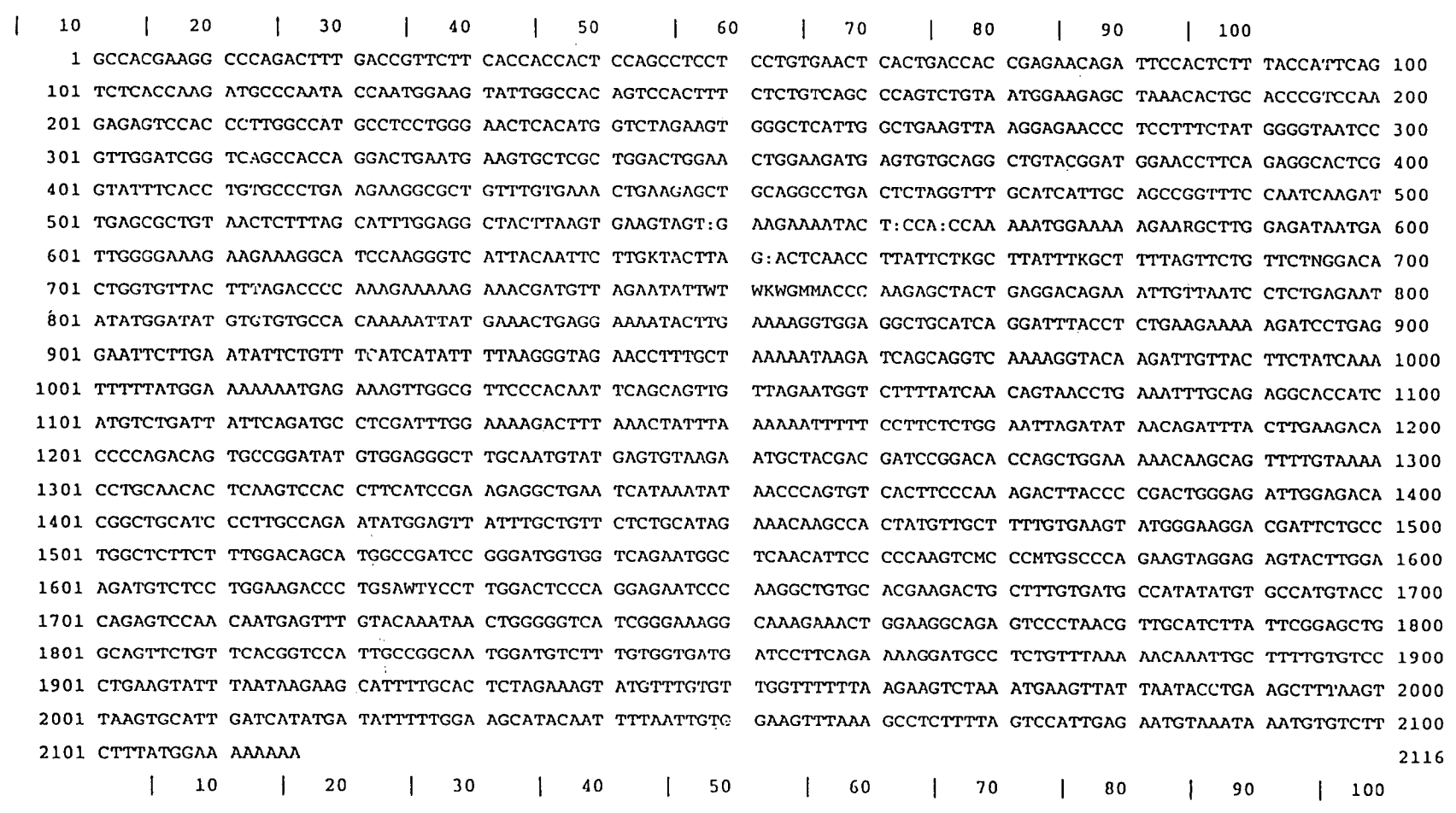

Cloned cDNAs obtained above in Example 1 were purified, amplified in *E. coli*, and the DNA obtained therefrom was subjected to sequence analysis using an ABI automatic sequencer. The cDNA sequences of clone 10 and of clone compl. 10 are shown in FIGS. 1 and 2 respectively. The amino acid sequence of the NAP polypeptide, as deduced from the cDNA sequence of clone compl. 10, is shown in FIG. 3.

Example 3

Expression of Cloned cDNAs and Interaction Between the Expressed Proteins

HeLa-Bujard cells were transfected with NEMO tagged with FLAG octapeptide sequence in pUHD10-3 based expression vector and constructs containing the open reading frame (ORF) of the selected clones fused to the Hemagglutinin (HA) (sequence encoding FLAG was introduced just in front of the site for insertion of NEMO) epitope. The cells were then grown for 24 hrs. in Dulbecco's Modified Eagle's Medium (DMEM) plus 10% calf serum with added 35S-Methionine and 35S-Cysteine. At the end of that incubation time, cells were lysed in radioimmune precipitation buffer (10 mM Tris-HCl, pH 7.5, 150 mM NaCl, 1% Nonidet P-40, 1% deoxycholate, 0.1% SDS, and 1 mM EDTA; 1 ml/5×105 cells), and the lysate was precleared by incubation with irrelevant rabbit antiserum and Protein G-Sepharose beads (Pharmacia, Sweden). Immunoprecipitation was performed by incubating aliquots of the lysate with anti-FLAG (purchased from Eastman Kodak Co.) or anti-HA (clone 12CA5, Field et al., 1988) monoclonal antibodies for 1 hour at 4° C. The expressed proteins were analysed on SDS-PAGE gel followed by autoradiography. The results of such experiments demonstrated that the partial cDNA clone 10 encoded a protein with a molecular weight of about 65 kDa.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Abe et al., "Specific inhibition of influenza virus RNA polymerase and nucleoprotein gene expression by liposomally encapsulated antisense phosphorothioate oligonucleotides in MDCK cells", *Antivir. Chem. Chemother.*, 9:253-62 (1998)

Adelman et al., "In vitro deletional mutagenesis for bacterial production of the 20,000-dalton form of human pituitary growth hormone", *DNA* 2:183-93 (1983)

Akagi et al., "Transcriptional activation of a hybrid promoter composed of cytomegalovirus enhancer and beta-actin/beta-globin gene in glomerular epithelial cells in vivo", *Kidney Int.*, 51:1265-9 (1997)

Artelt et al., "Vectors for efficient expression in mammalian fibroblastoid, myeloid and lymphoid cells via transfection or infection", *Gene*, 68:213-9 (1988)

Ausube et al., Current Protocols in Molecular Biology, Greene Publications and Wiley Interscience, (1987-2000)

Bai et al., "Gene transfer to vein graft wall by HVJ-liposome method: time course and localization of gene expression", *Ann. Thorac. Surg.*, 66:814-9 (1998)

Bazan, *Current Biology*, 3:603-606 (1993)

Berberich et al., "Cross-linking CD40 on B cells rapidly activates nuclear factor-kappa B", *J Immunol*, 153:4357-66 (1994)

Bochot et al., "Liposomes dispersed within a thermosensitive gel: a new dosage form for ocular delivery of oligonucleotides", *Pharm. Res.*, 15:1364-9 (1998)

Boldin et al., "Involvement of MACH, a novel MORT1/FADD-interacting protease, in Fas/APO-1- and TNF receptor-induced cell death", *Cell*, 85:803-815 (1996)

Boldin et al., "A novel protein that interacts with the death domain of Fas/APO1 contains a sequence motif related to the death domain", *J. Biol. Chem.* 270:7795-8 (1995)

Bonner et al., "Reduction in the rate of DNA reassociation by sequence divergence", *J. Mol. Biol.*, 81:123-135 (1973)

Boulianne et al., "Production of functional chimaeric mouse/human antibody", *Nature*, 312:643 (1984)

Cabilly et al., "Generation of antibody activity from immunoglobulin polypeptide chains produced in *Escherichia coli*", *Proc. Natl. Acad. Sci. USA*, 81:3273 (1984)

Cantor et al., *PNAS*, 90:10932 (1993)

Cao et al., "TRAF6 is a signal transducer for interleukin-1", *Nature*, 383:443-446 (1996)

Cao et al., "Lymphotactin gene-modified bone marrow dendritic cells act as more potent adjuvants for peptide delivery to induce specific antitumor immunity", *J. Immunol.*, 161:6238-44 (1998)

Capaccioli et al., "Cationic lipids improve antisense oligonucleotide uptake and prevent degradation in cultured cells and in human serum", *Biochem. Biophys. Res. Comm.*, 197:818-25 (1993)

Chen et al., *Ann. NY Acad. Sci.*, 660:271-3 (1992)

Coligan et al., Current Protocols in Protein Science, (1995-1999)

Coligan et al., Current Protocols in Protein Science, (1994-1996)

Creighton, "Proteins: Structure and Molecular Properties, W.H. Freeman & Co., San Francisco, Calif., 1983

Croston et al., "NF-kappa B activation by interleukin-1 (IL-1) requires an IL-1 receptor-associated protein kinase activity", *J Biol Chem.*, 28:16514-7 (1995)

Daniel et al., "Retroviral transfer of antisense sequences results in reduction of C-Abl and induction of apoptosis in hemopoietic cells", *J Biomed Sci.*, 5:383-94 (1998)

DiDonato et al., "Phosphorylation of I kappa B alpha precedes but is not sufficient for its dissociation from NF-kappa B", *Mol Cell Biol*, 15:1302-11 (1995)

Edamatsu et al., "Inducible high-level expression vector for mammalian cells, pEF-LAC carrying human elongation factor 1alpha promoter and lac operator", *Gene*, 187:289-94 (1997)

Edinger et al., "Use of GPR1, GPR15, and STRL33 as coreceptors by diverse human immunodeficiency virus type 1 and simian immunodeficiency virus envelope proteins", *Virology*, 249:367-78 (1998)

Elewaut et al., "A comparative phenotypical analysis of rheumatoid nodules and rheumatoid synovium with special reference to adhesion molecules and activation markers", *Ann Rheum Dis.*, 57:480-6 (1998)

Engelmann et al., "Antibodies to a soluble form of a tumor necrosis factor (TNF) receptor have TNF-like activity", *J. Biol. Chem.*, 265:14497-504 (1990)

Everett, et al., "The repeated GC-rich motifs upstream from the TATA box are important elements of the SV40 early promoter", *Nucleic Acids Res.*, 11:2447-64 (1983)

Fang et al., "A packaging system for SV40 vectors without viral coding sequences", *Anal. Biochem.*, 254:139-43 (1997)

Fields et al., *Nature* 340:245-246 (1989)

Flanagan, "Antisense comes of age", *Cancer Metastasis Rev.*, 17:169-76 (1998)

Furth et al., "Temporal control of gene expression in transgenic mice by a tetracycline-responsive promoter", *PNAS*, 91:9302-6 (1994)

Gerster et al., "Quantitative analysis of modified antisense oligonucleotides in biological fluids using cationic nanoparticles for solid-phase extraction", *Anal. Biochem.*, 262: 177-84 (1998)

Gilmore et al., "The I kappa B proteins: members of a multifunctional family", *Trends Genet.*, 9:427-33 (1993)

Graham et al., "Isolation and characterisation of the human lung NK-2 receptor gene using rapid amplification of cDNA ends", *Biochem Biophys Res Commun* 177, p. 8-16, 1991

Grell et al., "The transmembrane form of tumor necrosis factor is the prime activating ligand of the 80 kDa tumor necrosis factor receptor", *Cell*, 83:793-802 (1995)

Grilli et al., "NF-kappa B and Rel: participants in a multiform transcriptional regulatory system", *Int Rev Cytol.*, 143:1-62 (1993)

Griscelli et al., "Heart-specific targeting of beta-galactosidase by the ventricle-specific cardiac myosin light chain 2 promoter using adenovirus vectors", *Hum Gene Ther.*, 9:1919-28 (1998)

Guang-Lin et al., "Adenovirus-mediated gene transfer of CTLA41G gene results in prolonged survival of heart allograft", *Transplant Proc.*, 30:2923-4 (1998)

Guinot et al., "Antisense oligonucleotides: a new therapeutic approach", *Pathol. Biol.*, 46:347-54 (1998)

Hames et al., "Nucleic Acid Hybridisation: A Practical Approach", IRL Press, Washington, D.C., (1985)

Harlow et al., "Antibodies: A Laboratory Maunual", Cold Spring Harbor Laboratory (1988)

Hemmi et al., "The presence of human coxsackievirus and adenovirus receptor is associated with efficient adenovirus-mediated transgene expression in human melanoma cell cultures", *Hum Gene Ther.*, 9:2363-73 (1998)

Hsu et al., "The TNF receptor 1-associated protein TRADD signals cell death and NF-kappa B activation", *Cell*, 81:495-504 (1995)

Huang et al., *Nucleic Acids Res.*, 18:937-47 (1990) J. Biol. Chem., 49:183 (1921)

Joseph et al., "Optimization of an anti-HIV hairpin ribozyme by in vitro selection", *J. Biol. Chem.*, 268:24515 (1993)

Kanamaru et al., "Biological effects and cellular uptake of c-myc antisense oligonucleotides and their cationic liposome complexes", *J. Drug Target.*, 5:235-46 (1998)

Kim et al., *J. Controlled. Release*, 53:175-82 (1998)

Kita et al., "Growth inhibition of human pancreatic cancer cell lines by anti-sense oligonucleotides specific to mutated K-ras genes", *Int. J. Cancer,* 80:553-8 (1999)

Kohler et al., *Nature*, 256:495-497

Kondo et al., "Modulation of apoptosis by endogenous Bcl-xL expression in MKN-45 human gastric cancer cells", *Oncogene*, 17:2585-91 (1998)

Kumar et al., "Antisense RNA: function and fate of duplex RNA in cells of higher eukaryotes"; *Microbiol Mol Biol Rev.*, 62:1415-1434 (1998)

Langner et al., "Viral particles with heterologous binding motifs. An approach to specifically alter the tropism of the B-lymphotropic papovavirus", *Adv. Exp. Med. Biol.*, 451: 415-22 (1998)

McDonald et al., "CD30 ligation induces nuclear factor-kappa B activation in human T cell lines", *Eur J Immunol*, 25:2870-6 (1995)

Meinkoth et al., *Anal. Biochem.*, 70:75 (1984)

Meiri et al., "Memory and long-term potentiation (LTP) dissociated: normal spatial memory despite CA1 LTP elimination with Kv1.4 antisense", *PNAS*, 95:15037-15042 (1998)

Messing et al., "Third Cleveland Symposium on Macromolecules and Recombinant DNA", Editor A. Walton, Elsevier, Amsterdam (1981)

Meyer et al., J. Biol. Chem., 273:15621-7 (1998)

Mizuguchi et al., "Efficient gene transfer into mammalian cells using fusogenic liposome", Biochem. Biophys. Res. Commun., 218:402-7 (1996)

Morrison et al., "Chimeric human antibody molecules: mouse antigen-binding domains with human constant region domains", *Proc. Natl. Acad. Sci. USA*, 81:6851 (1984)

Mosialos et al., "The Epstein-Barr virus transforming protein LMP1 engages signaling proteins for the tumor necrosis factor receptor family", *Cell,* 80:389-399 (1995)

Muranishi et al., "Lipophilic peptides: synthesis of lauroyl thyrotropin-releasing hormone and its biological activity"; *Pharm. Research,* 8:649-52 (1991)

Nakamura et al., "A comparison of in vivo gene delivery methods for antisense therapy in ligament healing", *Gene Ther.,* 5:1455-61 (1998)

Narumi et al., "Adenovirus vector-mediated perforin expression driven by a glucocorticoid-inducible promoter inhibits tumor growth in vivo", *Am J Respir Cell Mol Biol.,* 19:936-941 (1998)

Pederson et al., "Combined cytosine deaminase expression, 5-fluorocytosine exposure, and radiotherapy increases cytotoxicity to cholangiocarcinoma cells", *J Gastrointest Surg.,* 2:283-91 (1998)

Nishida et al., "Adenovirus-mediated gene transfer to nucleus pulposus cells. Implications for the treatment of intervertebral disc degeneration", *Spine,* 23:2437-42, 1998

Noguchi et al., "Membrane fusion plays an important role in gene transfection mediated by cationic liposomes", *FEBS Lett.,* 433:169-73 (1998)

Paglia et al., "Gene transfer in dendritic cells, induced by oral DNA vaccination with *Salmonella typhimurium*, results in protective immunity against a murine fibrosarcoma", *Blood,* 92:3172-6 (1998)

Quattrone et al., *Biochemical,* 25 (1995)

Rensing-Ehl et al., "Fas/Apo-1 activates nuclear factor kappa B and induces interleukin-6 production", J. Inlamm., 45:161-174 (1995)

Rothe et al., "TRAF2-mediated activation of NF-kappa B by TNF receptor 2 and CD40", *Cell,* 78:681-692 (1994)

Rothe et al., "TRAF2-mediated activation of NF-kappa B by TNF receptor 2 and CD40", *Science,* 269:1424-1427 (1995)

Ruzicka et al., "Immuno-PCR with a commercially available avidin system", *Science,* 260:698-9 (1993)

Sambrook et al., "Molecular Cloning" A Labortory Manual", Cold Spring Harbor Laboratory (1989)

Sano et al., "A streptavidin-protein A chimera that allows one-step production of a variety of specific antibody conjugates", *Biotechniques* 9:1378-81 (1991)

Sano et al., *Science,* 258:120 (1992)

Scheidereit, "Signal transduction. Docking IkappaB kinases", *Nature,* 395:225-226 (1998)

Schek et al., "Definition of the upstream efficiency element of the simian virus 40 late polyadenylation signal by using in vitro analyses", *Mol Cell Biol.,* 5386-93 (1992)

Schulz et al., G. E., "Principles of Protein Structure Springer-Verlag", New York, N.Y. (1798)

Schwarzenberger et al., "IL-17 stimulates granulopoiesis in mice: use of an alternate, novel gene therapy-derived method for in vivo evaluation of cytokines", *J Immunol.,* 161:6383-9 (1998)

Shimayama et al., "Cleavage of the highly conserved hairpin-loop region of HIV-1 by synthetic ribozymes", *Nucleic Acids Symp Ser.*, 29:1/7-8 (1993)

Shoji et al., "Enhancement of anti-herpetic activity of antisense phosphorothioate oligonucleotides 5' end modified with geraniol", *J. Drug Target*, 5:261-73 (1998)

Shore et al., "Ribozyme-mediated cleavage of the BCRABL oncogene transcript: in vitro cleavage of RNA and in vivo loss of P210 protein-kinase activity", *Oncogene*, 8:3183-8 (1993)

Soni et al., "Biodistribution, stability, and antiviral efficacy of liposome-entrapped phosphorothioate antisense oligodeoxynucleotides in ducks for the treatment of chronic duck hepatitis B virus infection", *Hepatology*, 28:1402-10 (1998)

Soukchareun et al., *Bioconjug. Chem.*, 9:466-75 (1998)

Stanger et al., "RIP: a novel protein containing a death domain that interacts with Fas/APO-1 (CD95) in yeast and causes cell death", *Cell*, 81:513-523 (1995)

Stix, "Shutting down a gene. Antisense drug wins approval", *Sci. Amer.*, 279:46-50 (1998)

Sugawa et al., "An antisense EGFR oligodeoxynucleotide enveloped in Lipofectin induces growth inhibition in human malignant gliomas in vitro", *J. Neurooncol.*, 39:237-44 (1998)

Surfee et al., *Genes Dev*, 7:555-569 (1993)

Surinya et al., "Identification and characterization of a conserved erythroid-specific enhancer located in intron 8 of the human 5-aminolevulinate synthase 2 gene", *J Biol Chem.*, 273:16798-809 (1998)

Teoh et al., "Adenovirus vector-based purging of multiple myeloma cells", *Blood*, 92:4591-4601 (1998)

Thomsen, et al., "PNAS, 81:659-63 (1984)

Tirode et al., "A conditionally expressed third partner stabilizes or prevents the formation of a transcriptional activator in a three-hybrid system", *J. Biol. Chem.* 272: 22995-22999 (1997)

Tokushige, et al., "Comparison between cytomegalovirus promoter and elongation factor-1 alpha promoter-driven constructs in the establishment of cell lines expressing hepatitis C virus core protein", *J Virol Methods.*, 64:73-80 (1997)

Vandenabeele et al., *Trends Cell Biol.*, 5:392-400 (1995)

Veira et al., *Meth. Enzymol.* 153:3 (1987)

Waelti et al., "Delivery to cancer cells of antisense L-myc oligonucleotides incorporated in fusogenic, cationic-lipid-reconstituted influenza-virus envelopes (cationic virosomes)", *Int. J. Cancer*, 77:728-33 (1998)

Wahl et al., "Improved radioimaging and tumor localization with monoclonal F(ab')2", *J. Nucl. Med.*, 24:316-325 (1983)

Wallach, "A decade of accumulated knowledge and emerging answers", *Eur. Cytokine Net.* 7:713-724 (1996)

Wang, "Cyclic peptides incorporating 4-carboxyphenylalanine and phosphotyrosine are potent inhibitors of pp 60 (c-)(src)", *J. Controlled Release*, 53:39-48 (1998)

Weissig et al., "DQAsomes: a novel potential drug and gene delivery system made from Dequalinium", *Pharm. Res.*, 15:334-7 (1998)

Yamamoto et al., "Identification of a functional promoter in the long terminal repeat of Rous sarcoma virus", *Cell*, 22:787-97 (1980)

Yang et al., *Circ. Res.*, 83:552-9 (1998)

Yeh et al., "Inhibition of BMP receptor synthesis by antisense oligonucleotides attenuates OP-1 action in primary cultures of fetal rat calvaria cells", *J. Bone Miner. Res.*, 13:1870-1879 (1998)

Yotsuyanagi et al., "Cationic liposomes in gene delivery", *Nippon Rinsho*, 56:705-12 (1998)

Zacharia et al., "New reduced peptide bond substance P agonists and antagonists: effects on smooth muscle contraction", *Eur. J. Pharmacol.*, 203:353-7 (1991)

Zhang et al., *Clin Cancer Res.*, 4:2669-76 (1998)

Zhao et al., "Generating loss-of-function phenotypes of the fushi tarazu gene with a targeted ribozyme in *Drosophila*", *Nature*, 365:448-51 (1993)

---

What is claimed is:

1. An isolated protein which is capable of binding to tumor necrosis factor receptor-associated 2 protein (TRAF2), said protein comprising:
    (A) a polypeptide of SEQ ID NO:3; or
    (B) a variant that has no more than ten amino acid changes from the amino acid sequence of SEQ ID NO:3, wherein said variant is capable of binding to TRAF2.

2. The isolated protein of claim 1, which is a protein comprising the amino acid sequence of SEQ ID NO:3.

3. A composition comprising the isolated protein of claim 1 and a pharmaceutically acceptable excipient, diluent, or auxiliary agent.

4. A molecule having the binding portion of an antibody capable of binding to the portion of said isolated protein of claim 1 that is said polypeptide of (A) or said variant of (B).

5. The molecule of claim 4, which is an antibody.

6. The molecule of claim 5, wherein said antibody is a monoclonal antibody.

7. A composition comprising the molecule of claim 4, and a pharmaceutically acceptable excipient, diluent, or auxiliary agent.

8. An isolated protein in accordance with claim 1, wherein said protein and said variant are each capable of binding to a component of the NF-κB complex selected from the group consisting of IKappaB kinase complex associated protein (IKAP), IKappaB kinase-alpha (IKK-alpha), IKappaB kinase-beta (IKK-beta), IKappaB kinase-gamma (IKK-gamma) and NF-κB inducing kinase (NIK).

9. An isolated protein in accordance with claim 1, comprising a variant of the polypeptide of SEQ ID NO:3, which variant has no more than ten amino acid changes from the amino acid sequence of SEQ ID NO:3, and which variant is capable of binding to TRAF2.

10. The isolated protein of claim 1, wherein said variant of (B) has no more than five amino acid changes from the amino acid sequence of SEQ ID NO:3.

11. The isolated protein of claim 1, wherein each said change from the amino acid sequence of SEQ ID NO:3 is a conservative substitution selected from among the substitutions in the following list:

| Original Residue | Substitution |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu | or a conservative substitution that is an exchange within one of the following five groups:
Small aliphatic, nonpolar or

| | |
| --- | --- |
| slightly polar residues: | Ala, Ser, Thr, Pro, Gly; |
| Polar negatively charged residues and their amides: | Asp, Asn, Glu, Gln; |
| Polar, positively charged residues: | His, Arg, Lys; |
| Large aliphatic nonpolar residues: and | Met, Leu, Ile, Val, Cys; |
| Large aromatic residues: | Phe, Tyr, Trp. |

12. The isolated protein of claim 11, wherein said variant has no more than 5 of said amino acid changes from the amino acid sequence of SEQ ID NO:3.

13. A molecule having the binding portion of an antibody capable of binding to the polypeptide of SEQ ID NO:3.

14. The molecule of claim 13, which is an antibody.

15. The molecule of claim 14, wherein said antibody is a monoclonal antibody.

16. An isolated protein comprising:
    A) a polypeptide of SEQ ID NO: 3; or
    B) a variant that has no more than 10 amino acid changes from the amino acid sequence of SEQ ID NO:3.

17. The isolated protein of claim 16, wherein said variant has no more than 5 of said amino acid changes from the amino acid sequence of SEQ ID NO:3.

* * * * *

SEQUENCE LISTING

```
<160> NUMBER OF SEQ ID NOS: 4

<210> SEQ ID NO 1
<211> LENGTH: 2116
<212> TYPE: DNA
<213> ORGANISM: Homo sapiens
<220> FEATURE:
<221> NAME/KEY: misc_feature
<222> LOCATION: (549)..(549)
<223> OTHER INFORMATION: n is either a, c, g, or t.
<221> NAME/KEY: misc_feature
<222> LOCATION: (562)..(562)
<223> OTHER INFORMATION: n is either a, c, g, or t.
<221> NAME/KEY: misc_feature
<222> LOCATION: (566)..(566)
<223> OTHER INFORMATION: n is either a, c, g, or t.
<221> NAME/KEY: misc_feature
<222> LOCATION: (652)..(652)
<223> OTHER INFORMATION: n is either a, c, g, or t.
<221> NAME/KEY: misc_feature
<222> LOCATION: (695)..(695)
<223> OTHER INFORMATION: n is either a, c, g, or t.

<400> SEQUENCE: 1
gccacgaagg cccagacttt gaccgttctt caccaccact ccagcctcct cctgtgaact      60
cactgaccac cgagaacaga ttccactctt taccattcag tctcaccaag atgcccaata     120
```

```
ccaatggaag tattggccac agtccacttt ctctgtcagc ccagtctgta atggaagagc    180
taaacactgc acccgtccaa gagagtccac ccttggccat gcctcctggg aactcacatg    240
gtctagaagt gggctcattg gctgaagtta aggagaaccc tcctttctat ggggtaatcc    300
gttggatcgg tcagccacca ggactgaatg aagtgctcgc tggactggaa ctggaagatg    360
agtgtgcagg ctgtacggat ggaaccttca gaggcactcg gtatttcacc tgtgccctga    420
agaaggcgct gtttgtgaaa ctgaagagct gcaggcctga ctctaggttt gcatcattgc    480
agccggtttc caatcaagat tgagcgctgt aactctttag catttggagg ctacttaagt    540
gaagtagtng aagaaaatac tnccanccaa aaatggaaaa agaargcttg gagataatga    600
ttggggaaag aagaaaggca tccaagggtc attacaattc ttgktactta gnactcaacc    660
ttattctkgc ttatttkgct tttagttctg ttctnggaca ctggtgttac tttagacccc    720
aaagaaaaag aaacgatgtt agaatattwt wkwgmmaccc aagagctact gaggacagaa    780
attgttaatc ctctgagaat atatggatat gtgtgtgcca caaaaattat gaaactgagg    840
aaaatacttg aaaaggtgga ggctgcatca ggatttaccct ctgaagaaaa agatcctgag    900
gaattcttga atattctgtt tcatcatatt ttaagggtag aacctttgct aaaaataaga    960
tcagcaggtc aaaaggtaca agattgttac ttctatcaaa ttttttatgga aaaaaatgag   1020
aaagttggcg ttcccacaat tcagcagttg ttagaatggt cttttatcaa cagtaacctg   1080
aaatttgcag aggcaccatc atgtctgatt attcagatgc ctcgatttgg aaaagacttt   1140
aaactattta aaaattttt ccttctctgg aattagatat aacagattta cttgaagaca   1200
ccccagacag tgccggatat gtggagggct tgcaatgtat gagtgtaaga atgctacgac   1260
gatccggaca ccagctggaa aaacaagcag ttttgtaaaa cctgcaacac tcaagtccac   1320
cttcatccga agaggctgaa tcataaatat aacccagtgt cacttcccaa agacttaccc   1380
cgactgggag attggagaca cggctgcatc ccttgccaga atatggagtt atttgctgtt   1440
ctctgcatag aaacaagcca ctatgttgct tttgtgaagt atgggaagga cgattctgcc   1500
tggctcttct ttggacagca tggccgatcc gggatggtgg tcagaatggc tcaacattcc   1560
cccaagtcmc ccmtgsccca gaagtaggag agtacttgga agatgtctcc tggaagaccc   1620
tgsawtycct tggactccca ggagaatccc aaggctgtgc acgaagactg ctttgtgatg   1680
ccatatatgt gccatgtacc cagagtccaa caatgagttt gtacaaataa ctgggggtca   1740
tcgggaaagg caaagaaact ggaaggcaga gtccctaacg ttgcatctta ttcggagctg   1800
gcagttctgt tcacggtcca ttgccggcaa tggatgtctt tgtggtgatg atccttcaga   1860
aaaggatgcc tctgtttaaa aacaaattgc ttttgtgtcc ctgaagtatt taataagaag   1920
catttttgcac tctagaaagt atgtttgtgt tggttttta agaagtctaa atgaagttat   1980
taatacctga agctttaagt taagtgcatt gatcatatga tattttggaa agcatacaat   2040
tttaattgtc gaagtttaaa gcctcttttta gtccattgag aatgtaaata aatgtgtctt   2100
ctttatggaa aaaaaa                                                    2116
```

<210> SEQ ID NO 2
<211> LENGTH: 3715
<212> TYPE: DNA
<213> ORGANISM: Homo sapiens
<220> FEATURE:
<221> NAME/KEY: misc_feature
<222> LOCATION: (18)..(18)
<223> OTHER INFORMATION: n is either a, c, g, or t.
<221> NAME/KEY: misc_feature
<222> LOCATION: (22)..(22)

```
<223> OTHER INFORMATION: n is either a, c, g, or t.
<221> NAME/KEY: misc_feature
<222> LOCATION: (756)..(756)
<223> OTHER INFORMATION: n is either a, c, g, or t.
<221> NAME/KEY: misc_feature
<222> LOCATION: (1348)..(1348)
<223> OTHER INFORMATION: n is either a, c, g, or t.

<400> SEQUENCE: 2
```

| | | | | | |
|---|---|---|---|---|---|
| ggggttttct | tttacacntc | tncggtaccg | aactcggatc | cactagtaac | gggccgccag | 60 |
| tgtgctggaa | attcggcacg | agggtgtggg | gagccggggc | cggcccggga | cgcgggctgg | 120 |
| ggagccgggg | cgaggggcga | cgccccgccg | cccgagtttc | ccccttttcta | gggtgaggat | 180 |
| ggttctacac | agccacccgg | agttccttag | ttgaaaggtg | cgccctgctg | tgacagaatg | 240 |
| tggtaattgt | aatctttaac | attttcatgt | aaaacatatt | tcctgatcat | ctttccattg | 300 |
| tcttcatgga | aaattgataa | atatttgtgc | cttccaactc | tcgtcttggt | tgaatgactt | 360 |
| catcttaata | caacatggac | accacgttgc | tgaaaacatg | ctttgggact | gccactgaat | 420 |
| ttatcttttg | cggttttatg | acaaagttat | tagtagtttc | ccttttttga | attagtatt | 480 |
| tgaagttaat | atcacaatga | gttcaggctt | atggagccaa | gaaaaagtca | cttcaccccta | 540 |
| ctgggaagag | cggattttt | acttgcttct | tcaagaatgc | agcgttacag | acaaacaaac | 600 |
| acaaagctc | cttaaagtac | cgaagggaag | tataggacag | tatattcaag | atcgttctgt | 660 |
| ggggcattca | aggattcctt | ctgcaaaagg | caagaaaaat | cagattggat | taaaaattct | 720 |
| agagcaacct | catgcagttc | tctttgttga | tgaaanggat | gttgtagaga | taaatgaaaa | 780 |
| gttcacagag | ttacttttgg | caattaccaa | ttgtgaggag | aggttcagcc | tgtttaaaaa | 840 |
| cagaaacaga | ctaagtaaag | gcctccaaat | agacgtgggc | tgtcctgtga | aagtacagct | 900 |
| gagatctggg | gaagaaaaat | ttcctggagt | tgtacgcttc | agaggacccc | tgttagcaga | 960 |
| gaggacagtc | tccggaatat | tctttggagt | tgaattgctg | gaagaaggtc | gtggtcaagg | 1020 |
| tttcactgac | ggggtgtacc | aagggaaaca | gcttttcag | tgtgatgaag | attgtggcgt | 1080 |
| gtttgttgca | ttggacaagc | tagaactcat | agaagatgat | gacactgcat | tggaaagtga | 1140 |
| ttacgcaggt | cctggggaca | caatgcaggt | cgaacttcct | cctttggaaa | taaactccag | 1200 |
| agtttctttg | aagggtggag | aaacaataga | atctggaaca | gttatattct | gtgatgtttt | 1260 |
| gccaggaaaa | gaaagcttag | gatattttgt | tggtgtggac | atggataacc | ctattggcaa | 1320 |
| ctgggatgga | agatttgatg | gagtgcanct | ttgtagttt | gcgtgtgttg | aaagtacaat | 1380 |
| tctattgcac | atcaatgata | tcatcccaga | gagtgtgacg | caggaaagga | ggcctcccaa | 1440 |
| acttgccttt | atgtcaagag | gtgttgggga | caaaggttca | tccagtcata | ataaaccaaa | 1500 |
| ggctacagga | tctacctcag | accctggaaa | tagaamcaga | tctgaattat | tttataccttt | 1560 |
| aaatgggtct | tctgttgact | cacaaccaca | atccaaatca | aaaatacat | ggtacattga | 1620 |
| tgaagttgca | gaagaccctg | caaatctct | tacagagata | tctacagact | ttgaccgttc | 1680 |
| ttcaccacca | ctccagcctc | ctcctgtgaa | ctcactgacc | accgagaaca | gattccactc | 1740 |
| tttaccattc | agtctcacca | agatgcccaa | taccaatgga | agtattggcc | acagtccact | 1800 |
| ttctctgtca | gcccagtctg | taatggaaga | gctaaacact | gcaccccgtcc | aagagagtcc | 1860 |
| acccttggcc | atgcctcctg | ggaactcaca | tggtctagaa | gtgggctcat | tggctgaagt | 1920 |
| taaggagaac | cctcctttct | atggggtaat | ccgttggatc | ggtcagccac | caggactgaa | 1980 |
| tgaagtgctc | gctggactgg | aactggaaga | tgagtgtgca | ggctgtacgg | atggaacctt | 2040 |
| cagaggcact | cggtatttca | cctgtgccct | gaagaaggcg | ctgtttgtga | aactgaagag | 2100 |

-continued

```
ctgcaggcct gactctaggt ttgcatcatt gcagccggtt tccaatcaga ttgagcgctg    2160
taactcttta gcatttggag gctacttaag tgaagtagta aagaaaata ctccaccaaa    2220
aatggaaaaa gaaggcttgg agataatgat tgggaagaag aaaggcatcc agggtcatta    2280
caattcttgt tacttagact caaccttatt ctgcttattt gcttttagtt ctgttctgga    2340
cactgtgtta cttagaccca agaaaagaa cgatgtagaa tattatagtg aaacccaaga    2400
gctactgagg acagaaattg ttaatcctct gagaatatat ggatatgtgt gtgccacaaa    2460
aattatgaaa ctgaggaaaa tacttgaaaa ggtggaggct gcatcaggat ttacctctga    2520
agaaaaagat cctgaggaat tcttgaatat tctgtttcat catattttaa gggtagaacc    2580
tttgctaaaa ataagatcag caggtcaaaa ggtacaagat tgttacttct atcaaatttt    2640
tatggaaaaa aatgagaaag ttggcgttcc cacaattcag cagttgttag aatggtcttt    2700
tatcaacagt aacctgaaat ttgcagaggc accatcatgt ctgattattc agatgcctcg    2760
atttggaaaa gactttaaac tatttaaaaa aatttttcct tctctggaat taaatataac    2820
agatttactt gaagacactc ccagacagtg ccggatatgt ggagggcttg caatgtatga    2880
gtgtagagaa tgctacgacg atccggacat ctcagctgga aaaatcaagc agttttgtaa    2940
aacctgcaac actcaagtcc accttcatcc gaagaggctg aatcataaat ataacccagt    3000
gtcacttccc aaagacttac ccgactggga ctggagacac ggctgcatcc cttgccagaa    3060
tatggagtta tttgctgttc tctgcataga acaagccac tatgttgctt ttgtgaagta    3120
tgggaaggac gattctgcct ggctcttctt tgacagcatg gccgatcggg atggtggtca    3180
gaatggcttc aacattcctc aagtcacccc atgcccagaa gtaggagagt acttgaagat    3240
gtctctggaa gacctgcatt ccttggactc caggagaatc caaggctgtg cacgaagact    3300
gctttgtgat gcatatatgt gcatgtacca gagtccaaca atgagtttgt acaaataact    3360
ggggtcatcg ggaaaggcaa agaaactgaa ggcagagtcc taacgttgca tcttattcga    3420
gctggcagtt ctgttcacgt ccattgccgg caatggatgt ctttgtggtg atgatccttc    3480
agaaaaggat gcctctgttt aaaaacaaat tgcttttgtg tccctgaagt atttaataag    3540
aagcattttg cactctagaa agtatgtttg tgttggtttt ttaagaagtc taaatgaagt    3600
tattaatacc tgaagcttta agttaagtgc attgatcata tgatattttt ggaagcatac    3660
aattttaatt gtggaagttt aaagcctctt ttagtccatt gagaatgtaa ataaa         3715
```

<210> SEQ ID NO 3
<211> LENGTH: 949
<212> TYPE: PRT
<213> ORGANISM: Homo sapiens

<400> SEQUENCE: 3

```
Met Ser Ser Gly Leu Trp Ser Gln Glu Lys Val Thr Ser Pro Tyr Trp
 1               5                  10                  15

Glu Glu Arg Ile Phe Tyr Leu Leu Leu Gln Glu Cys Ser Val Thr Asp
            20                  25                  30

Lys Gln Thr Gln Lys Leu Leu Lys Val Pro Lys Gly Ser Ile Gly Gln
        35                  40                  45

Tyr Ile Gln Asp Arg Ser Val Gly His Ser Arg Ile Pro Ser Ala Lys
    50                  55                  60

Gly Lys Lys Asn Gln Ile Gly Leu Lys Ile Leu Glu Gln Pro His Ala
65                  70                  75                  80

Val Leu Phe Val Asp Glu Asp Val Val Glu Ile Asn Glu Lys Phe Thr
```

-continued

```
                    85                  90                  95
Glu Leu Leu Leu Ala Ile Thr Asn Cys Glu Glu Arg Phe Ser Leu Phe
                100                 105                 110
Lys Asn Arg Asn Arg Leu Ser Lys Gly Leu Gln Ile Asp Val Gly Cys
                115                 120                 125
Pro Val Lys Val Gln Leu Arg Ser Gly Glu Glu Lys Phe Pro Gly Val
            130                 135                 140
Val Arg Phe Arg Gly Pro Leu Leu Ala Glu Arg Thr Val Ser Gly Ile
145                 150                 155                 160
Phe Phe Gly Val Glu Leu Leu Glu Glu Gly Arg Gly Gln Gly Phe Thr
                165                 170                 175
Asp Gly Val Tyr Gln Gly Lys Gln Leu Phe Gln Cys Asp Glu Asp Cys
                180                 185                 190
Gly Phe Val Ala Leu Asp Lys Leu Glu Leu Ile Glu Asp Asp Asp Thr
            195                 200                 205
Ala Leu Glu Ser Asp Tyr Ala Gly Pro Gly Asp Thr Met Gln Val Glu
        210                 215                 220
Leu Pro Pro Leu Glu Ile Asn Ser Arg Val Ser Leu Lys Gly Gly Glu
225                 230                 235                 240
Thr Ile Glu Ser Gly Thr Val Ile Phe Cys Asp Val Leu Pro Gly Lys
                245                 250                 255
Glu Ser Leu Gly Tyr Phe Val Gly Val Asp Met Asp Asn Pro Ile Gly
                260                 265                 270
Asn Trp Asp Gly Arg Phe Asp Gly Val Leu Cys Ser Phe Ala Cys Val
            275                 280                 285
Glu Ser Thr Ile Leu Leu His Ile Asn Asp Ile Ile Pro Glu Ser Val
        290                 295                 300
Thr Gln Glu Arg Arg Pro Pro Lys Leu Ala Phe Met Ser Arg Gly Val
305                 310                 315                 320
Gly Asp Lys Gly Ser Ser His Asn Lys Pro Lys Ala Thr Gly Ser
                325                 330                 335
Thr Ser Asp Pro Gly Asn Arg Arg Ser Glu Leu Phe Tyr Thr Leu Asn
                340                 345                 350
Gly Ser Ser Val Asp Ser Gln Pro Gln Ser Lys Ser Lys Asn Thr Trp
            355                 360                 365
Tyr Ile Asp Glu Val Ala Glu Asp Pro Ala Lys Ser Leu Thr Glu Ile
        370                 375                 380
Ser Thr Asp Phe Asp Arg Ser Pro Pro Leu Gln Pro Pro Val
385                 390                 395                 400
Asn Ser Leu Thr Thr Glu Asn Arg Phe His Ser Leu Pro Phe Ser Leu
                405                 410                 415
Thr Lys Met Pro Asn Thr Asn Gly Ser Ile Gly His Ser Pro Leu Ser
                420                 425                 430
Leu Ser Ala Gln Ser Val Met Glu Glu Leu Asn Thr Ala Pro Val Gln
            435                 440                 445
Glu Ser Pro Pro Leu Ala Met Pro Pro Gly Asn Ser His Gly Leu Glu
        450                 455                 460
Val Gly Ser Leu Ala Glu Val Lys Glu Asn Pro Pro Phe Tyr Gly Val
465                 470                 475                 480
Ile Arg Trp Ile Gly Gln Pro Pro Gly Leu Asn Glu Val Leu Ala Gly
                485                 490                 495
Leu Glu Leu Glu Asp Glu Cys Ala Gly Cys Thr Asp Gly Thr Phe Arg
                500                 505                 510
```

-continued

```
Gly Thr Arg Tyr Phe Thr Cys Ala Leu Lys Lys Ala Leu Phe Val Lys
            515                 520                 525
Leu Lys Ser Cys Arg Pro Asp Ser Arg Phe Ala Ser Leu Gln Pro Val
        530                 535                 540
Ser Asn Gln Ile Glu Arg Cys Asn Ser Leu Ala Phe Gly Gly Tyr Leu
545                 550                 555                 560
Ser Glu Val Val Glu Glu Asn Thr Pro Pro Lys Met Glu Lys Glu Gly
                565                 570                 575
Leu Glu Ile Met Ile Gly Lys Lys Gly Ile Gln Gly His Tyr Asn
            580                 585                 590
Ser Cys Tyr Leu Asp Ser Thr Leu Phe Cys Leu Phe Ala Phe Ser Ser
        595                 600                 605
Val Leu Asp Thr Val Leu Leu Arg Pro Lys Glu Lys Asn Asp Val Glu
    610                 615                 620
Tyr Tyr Ser Glu Thr Gln Glu Leu Leu Arg Thr Glu Ile Val Asn Pro
625                 630                 635                 640
Leu Arg Ile Tyr Gly Tyr Val Cys Ala Thr Lys Ile Met Lys Leu Arg
                645                 650                 655
Lys Ile Leu Glu Lys Val Glu Ala Ala Ser Gly Phe Thr Ser Glu Glu
            660                 665                 670
Lys Asp Pro Glu Glu Phe Leu Asn Ile Leu Phe His His Ile Leu Arg
        675                 680                 685
Val Glu Pro Leu Leu Lys Ile Arg Ser Ala Gly Gln Lys Val Gln Asp
    690                 695                 700
Cys Tyr Phe Tyr Gln Ile Phe Met Glu Lys Asn Glu Lys Val Gly Val
705                 710                 715                 720
Pro Thr Ile Gln Gln Leu Leu Glu Trp Ser Phe Ile Asn Ser Asn Leu
                725                 730                 735
Lys Phe Ala Glu Ala Pro Ser Cys Leu Ile Ile Gln Met Pro Arg Phe
            740                 745                 750
Gly Lys Asp Phe Lys Leu Phe Lys Lys Ile Phe Pro Ser Leu Glu Leu
        755                 760                 765
Asn Ile Thr Asp Leu Leu Glu Asp Thr Pro Arg Gln Cys Arg Ile Cys
    770                 775                 780
Gly Gly Leu Ala Met Tyr Glu Cys Arg Glu Cys Tyr Asp Asp Pro Asp
785                 790                 795                 800
Ile Ser Ala Gly Lys Ile Lys Gln Phe Cys Lys Thr Cys Asn Thr Gln
                805                 810                 815
Val His Leu His Pro Lys Arg Leu Asn His Lys Tyr Asn Pro Val Ser
            820                 825                 830
Leu Pro Lys Asp Leu Pro Asp Trp Asp Trp Arg His Gly Cys Ile Pro
        835                 840                 845
Cys Gln Asn Met Glu Leu Phe Ala Val Leu Cys Ile Glu Thr Ser His
    850                 855                 860
Tyr Val Ala Phe Val Lys Tyr Gly Lys Asp Asp Ser Ala Trp Leu Phe
865                 870                 875                 880
Phe Asp Ser Met Ala Asp Arg Asp Gly Gly Gln Asn Gly Phe Asn Ile
                885                 890                 895
Pro Gln Val Thr Pro Cys Pro Glu Val Gly Glu Tyr Leu Lys Met Ser
            900                 905                 910
Leu Glu Asp Leu His Ser Leu Asp Ser Arg Arg Ile Gln Gly Cys Ala
        915                 920                 925
```

-continued

```
Arg Arg Leu Leu Cys Asp Ala Tyr Met Cys Met Tyr Gln Ser Pro Thr
        930             935             940
Met Ser Leu Tyr Lys
945

<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
cggtggtcag tgagttcaca ggagg                                          25
```